United States Patent
Belter et al.

(10) Patent No.: US 10,219,919 B2
(45) Date of Patent: Mar. 5, 2019

(54) MULTI-GRASP PROSTHETIC HAND

(71) Applicant: Yale University, New Haven, CT (US)

(72) Inventors: Joseph Thomas Belter, New Haven, CT (US); Aaron Michael Dollar, New Haven, CT (US); Michael Leddy, New Haven, CT (US); Kevin Dale Gemmell, Jr., San Diego, CA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/240,819

(22) Filed: Aug. 18, 2016

(65) Prior Publication Data

US 2017/0049583 A1 Feb. 23, 2017

Related U.S. Application Data

(60) Provisional application No. 62/206,479, filed on Aug. 18, 2015.

(51) Int. Cl.
*A61F 2/54* (2006.01)
*A61F 2/58* (2006.01)
*A61F 2/50* (2006.01)
*A61F 2/68* (2006.01)
*A61F 2/72* (2006.01)
*B33Y 10/00* (2015.01)
*A61F 2/70* (2006.01)
*A61F 5/56* (2006.01)

(52) U.S. Cl.
CPC ............ *A61F 2/583* (2013.01); *A61F 2/5044* (2013.01); *A61F 2/5046* (2013.01); *A61F 2/586* (2013.01); *A61F 2/68* (2013.01); *A61F 2/72* (2013.01); *A61F 2002/5075* (2013.01); *A61F 2002/5093* (2013.01); *A61F 2002/6872* (2013.01); *A61F 2002/701* (2013.01); *A61F 2005/563* (2013.01); *B33Y 10/00* (2014.12)

(58) Field of Classification Search
CPC .... A61F 2/54; A61F 2/58; A61F 2/583; A61F 2/586; A61F 2002/587
USPC ...................................... 623/57–65
See application file for complete search history.

(56) References Cited

U.S. PATENT DOCUMENTS

| 5,092,646 | A | * | 3/1992 | Smallridge | ............... B25J 9/104 254/278 |
| 2013/0253705 | A1 | * | 9/2013 | Goldfarb | ................. A61F 2/583 700/260 |
| 2015/0230941 | A1 | * | 8/2015 | Jury | ........................ A61F 2/583 623/64 |

FOREIGN PATENT DOCUMENTS

| WO | WO 03017880 A1 * | 3/2003 | ............. A61F 2/583 |
| WO | WO 2010018358 A2 * | 2/2010 | ............... A61F 2/54 |

* cited by examiner

*Primary Examiner* — Marcia Watkins
(74) *Attorney, Agent, or Firm* — Riverside Law LLP

(57) ABSTRACT

The present invention provides a prosthetic hand capable of multiple grasp types. The prosthetic finger units are under-actuated both within and between the finger units using a differential mechanism arrangement. The locking movement of the prosthetic thumb unit is coupled to the differential mechanism. As the user repositions the prosthetic thumb unit, the differential mechanism is effected as to alter both the initial positions and force distribution of the prosthetic finger units. The present invention further provides an additive manufacturing molding method for making the same.

13 Claims, 35 Drawing Sheets

Finger Tendon Force Ratios

| Grasp Type | Body-powered Cable Force | Little Finger tendon force | Ring Finger tendon force | Middle Finger tendon force | Index Finger tendon force |
|---|---|---|---|---|---|
| Power Grasp | x | 0.25x | 0.25x | 0.25x | 0.25x |
| Precision Grasp | x | y | y | y | 0.57x - 1.29y |

Figure 25

Finger Stiffness to Weight Ratio

| Specimen | Weight (g) | Density (g/cm^3) | Yield Stress (MPa) | Max Strength / Weight Ratio (GPa*cm^3/g) | Max Stiffness / Weight Ratio (GPa*cm^3/g) |
|---|---|---|---|---|---|
| *Sparse Printed ABS* | 17.5 | 0.71 | 26.3 | 0.037 | 2.03 |
| *Solid Printed ABS* | 23.3 | 0.95 | 43.5 | 0.046 | 2.08 |
| *PB 400 Epoxy Foam* | 9.3 | 0.39 | 6.3 | 0.016 | 1.33 |
| *Two Layer 2x2 Carbon Twill - PB 400 EEF* | 11.3 | 0.46 | 56.4* | 0.123 | 16.51 |
| *6061 Aluminum*** | 65.2 | 2.70 | 276 | 0.102 | 25.52 |

*Yield stress was equal to fracture stress, **Calculated based on (ASTM D790, "Standard test method of flexural properties of unreinforced and reinforced Plastics and electrically insolating materials", ASTM.org, ASTM International)

Figure 31

Finger Weights

| Finger Composition | Weight (g) |
|---|---|
| Sparse Printed ABS | 13.2 |
| Solid Printed ABS | 14.5 |
| PB 400 Expanding Epoxy Foam | 8.5 |
| Carbon and PB400 Laminate | 8.6 |
| 6061 Aluminum (Solid) | 31.6 |

Figure 35

MULTI-GRASP PROSTHETIC HAND

CROSS-REFERENCE TO RELATED APPLICATIONS

This application claims priority to U.S. Provisional Patent Application No. 62/206,479 filed Aug. 18, 2015, the contents of which are incorporated by reference herein in its entirety.

STATEMENT REGARDING FEDERALLY SPONSORED RESEARCH OR DEVELOPMENT

This invention was made with government support under grant nos. 1317976 and 0953856 awarded by the National Science Foundation and grant nos. W81XWH-13-2-0073 and W81XWH-10-1-0921 awarded by the United States Army Medical Research & Material Command. The government has certain rights in the invention.

BACKGROUND OF THE INVENTION

The current state-of-the-art in anthropomorphic prosthetic hands, such as the iLimb, Bebionic, and Vincent designs, generally use an individual actuator for each finger in order to enable multiple grasping behaviours and postures. The ability to utilize various grasp types helps to improve the hold on various shaped objects or to position the hand in the appropriate posture to facilitate as wide a range of tasks as possible. Although each style of prosthetic has its own strategy, these devices rely on myoelectric sequences, co-contractions or patterns to preselect the type of grasp. Many researchers have studied possible strategies to give quick and easy grasp selection including state-space trees and highly tuned pattern recognition software. The large variation in grasp types is what gives these myoelectric hands increased utility over single degree of freedom myoelectric hands.

Despite achieving various grasp types, it is still difficult for users of myoelectric hands to modulate grip force due to the lack of feedback from the hand. Body-powered devices, which are actuated through the upper arm or shoulders, are much easier to operate in terms of modulating grip force. This is largely due to the "feel" of the grasp as a result of the force exerted on the shoulder from the harness. They are also simpler and more robust than the multi-degree of freedom offered by myoelectric devices. Until now, body-powered devices have been restricted to operating a single degree of freedom, as in the body-powered split hook, or to open and close an anthropomorphic hand in a single grasp motion.

A major difficulty in the actuation of body-powered anthropomorphic prosthetic hands lies in the distribution of force from the body-powered cable to the five fingers. The simplest method is to couple all the fingers together into a single combined motion. This results in a single degree of freedom terminal device that is capable of performing a single grasp type. Although it is mechanically simple, other coupling methods can be used to allow for multiple grasping types and adaptive grip behaviour. Underactuation has shown advantages in robotic grasping, including better power grasping, more adaptive behaviour to various object types and shapes, and an increase in the number of contacts made on objects (Ohdner L U et al., Int J Robot Res, 2014). Many researchers have turned to relying on underactuated adaptive transmission systems to distribute load from a single actuation source to multiple fingers of the hand (Baril M et al., Proceedings of the ASME/IDETC/CEI, 2010).

There is a need in the art for a prosthetic hand capable of multiple grasp types with improved grasping performance. The present invention meets this need.

SUMMARY OF THE INVENTION

The present invention provides a prosthetic hand capable of multiple grasp types. The prosthetic finger units are underactuated both within and between the finger units using a differential mechanism arrangement. The present invention further provides an additive manufacturing molding method for making the same.

In one aspect, the invention relates to a prosthetic hand device. The device comprises a hand frame having a differential mechanism connected to an actuable index finger unit, at least one actuable secondary finger unit and an actuable thumb unit, wherein the actuable thumb unit includes a plurality of lockable positions, wherein each lockable position corresponds to a different grasping configuration of the prosthetic hand.

In one embodiment, the differential mechanism comprises: a first bar having a pin joint at its midpoint and is coupled to at least one tendon line of the at least one secondary finger unit; and a second bar coupled to an index finger tendon line and an index finger orientation cable at one end, to a thumb orientation cable at the opposite end, to a main actuation cable along its length, and to the pin joint of the first bar at a point between the second bar's midpoint and the thumb orientation cable coupling; wherein movement of the first bar opens and closes the at least one secondary finger unit at the same time; wherein movement of the second bar opens and closes the index finger unit independently; and wherein the orientation of the thumb unit alters the configuration of the differential mechanism by applying tension on the thumb orientation cable and the index finger orientation cable.

In one embodiment, the at least one secondary finger unit, index finger unit and the thumb unit are passively held open by helical torsion springs and elastic flexure joints. In one embodiment, the at least one secondary finger unit, index finger unit and the thumb unit are connected to the device using removable pins.

In one embodiment, the thumb unit is lockable into alignment with a secondary finger unit for a power grasp. In one embodiment, actuation of the prosthetic hand opens and closes the thumb unit, the at least one secondary finger unit, and the index finger unit.

In one embodiment, the thumb unit is lockable into alignment with the index finger unit for a precision grasp. In one embodiment, the at least one secondary finger is locked in a closed position and actuation of the prosthetic hand opens and closes the thumb unit and the index finger unit.

In one embodiment, the thumb unit is lockable into alignment with the side of the hand for a lateral grasp. In one embodiment, the at least one secondary finger unit and the index finger unit are locked in a closed position and actuation of the prosthetic hand opens and closes the thumb unit.

In one embodiment, the prosthetic hand is actuated by a body-powered harness. In one embodiment, the prosthetic hand is actuated by myoelectric control. In various embodiments, the prosthetic hand further comprises a grasp locking mechanism comprising a cable wrapped around a unidirectional rotating surface using friction to hold a grasp in place until the actuation is relaxed. In one embodiment, the unidirectional rotating surface is a textured and contoured capstan pulley.

In another aspect, the invention relates to a method of fabricating prosthetic components. The method comprises the steps of: forming a first mold and a second mold for fabricating grip pads; fabricating the grip pads by joining the first mold to the second mold; removing the second mold from the first mold while retaining the grip pads in the first mold; forming a third mold for fabricating the prosthetic component structural shell; fabricating the structural shell using the third mold; inserting internal mechanical components to the structural shell in the third mold; and fabricating the prosthetic component by joining the first mold having grip pads to the third mold having the structural shell and internal mechanical components.

In one embodiment, the molds are designed using computer aided design to fit a user's individual anatomy. In one embodiment, the molds are formed using 3D printing. In one embodiment, the grip pads are fabricated from urethane. In one embodiment, the structural shell is fabricated from carbon fiber and epoxy resin. In one embodiment, the prosthetic component is fabricated by injecting expanding epoxy foam into the mold space.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

FIG. 21, comprising

FIG. 24, comprising

FIG. 25 is a table listing exemplary finger tendon force ratios for different coupling methods.

FIG. 26, comprising FIG. 26A—power grasp; FIG. 26B—precision grasp; and FIG. 26C—lateral grasp. Each position alters the internal coupling of the body-powered cable to the fingers to optimize for each grasp type.

FIG. 31 is a table showing the stiffness to weight ratio for each specimen.

FIG. 35 is a table showing the weight of fingers fabricated with each respective material.

DETAILED DESCRIPTION

Figure 1:
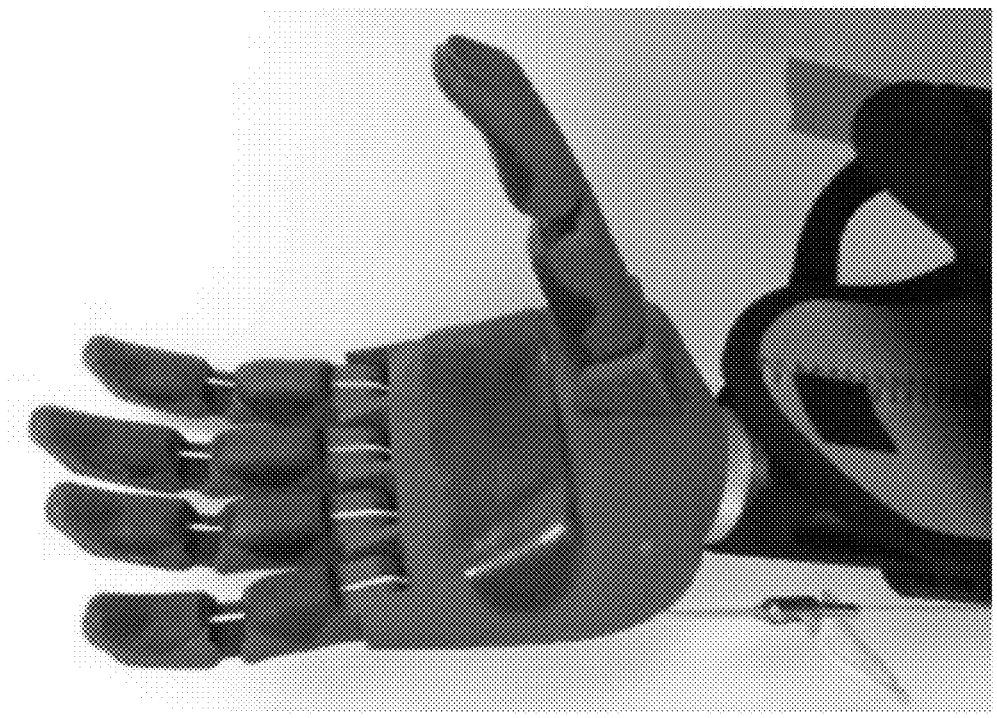
FIG. 1 depicts an exemplary prosthetic hand. The hand depicted is a right hand.

The present invention provides a prosthetic hand capable of multiple grasp types and methods for making the same. The prosthetic hand is amenable to body-powered actuation as well as myoelectric actuation.

The present invention has an anthropomorphic appearance and a lockable thumb unit. The finger units are under-actuated both within and between the finger units using a differential mechanism. In one embodiment, the differential mechanism is a double balance bar arrangement. The locking movement of the thumb unit is coupled to the double balance bar. As the user repositions the thumb unit, the double balance bar is effected as to alter both the initial positions and force distribution of the finger units.

The present invention provides an additive manufacturing molding method for the fabrication of the prosthetic hand. The method relates to a layering of molded carbon-fiber shells with epoxy expanded foam and integrated elastic features as flexible joints and as variable stiffness grip surfaces.

Definitions

It is to be understood that the figures and descriptions of the present invention have been simplified to illustrate elements that are relevant for a clear understanding of the present invention, while eliminating, for the purpose of clarity, many other elements found in typical prosthetic hands. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

The Prosthetic Hand

In one embodiment, the invention provides a prosthetic hand comprising a differential mechanism and an independently lockable thumb unit. In one embodiment, the differential mechanism is a double balance bar. In various embodiments, the prosthetic hand comprises a power grasp configuration, a precision grasp configuration, and a lateral grasp configuration, wherein each configuration is determined by the locking position of the thumb unit.

Figure 2:
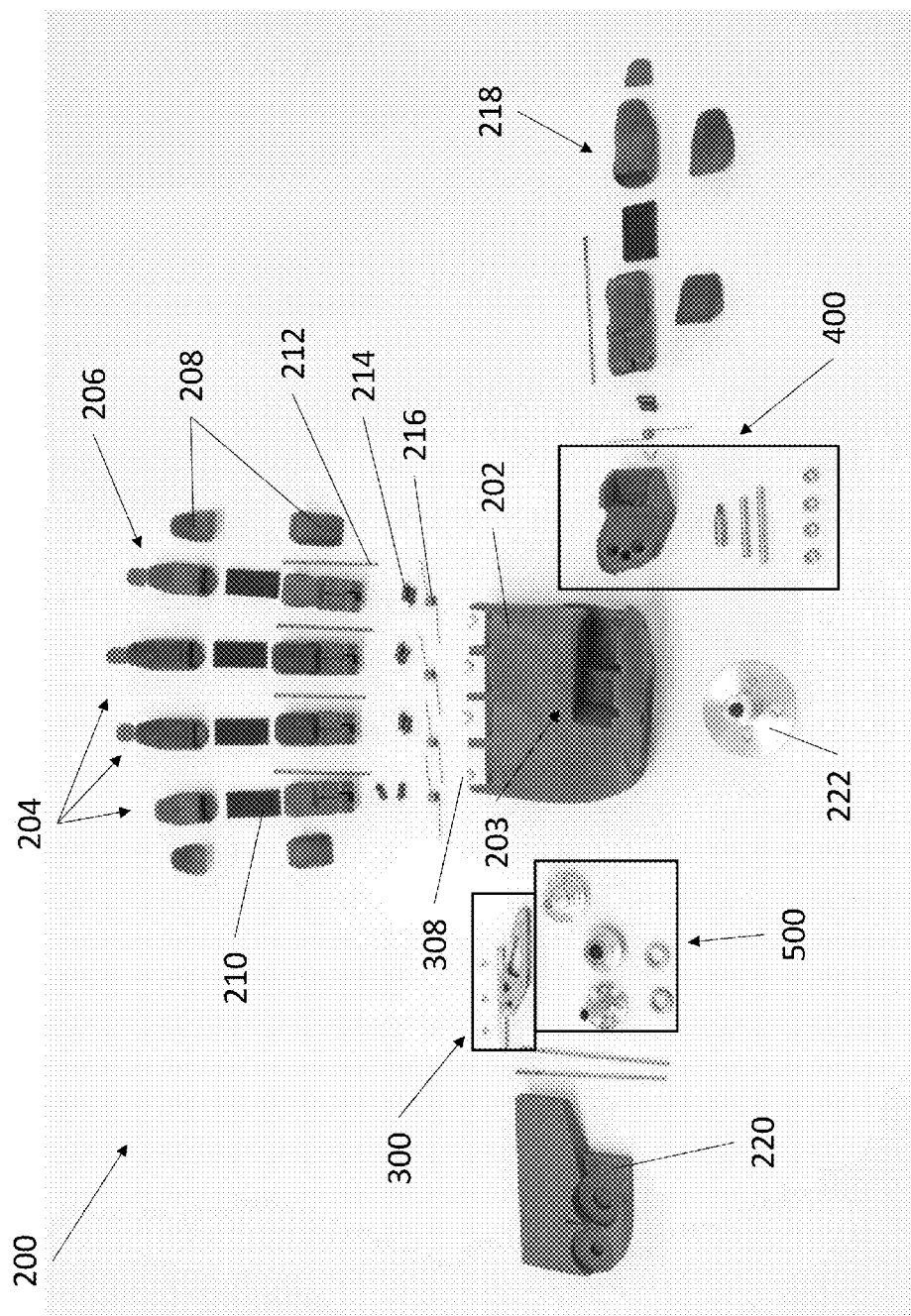
FIG. 2 depicts an exploded view of the exemplary prosthetic hand of FIG. 1. The hand depicted is a right hand.
Figure 29:
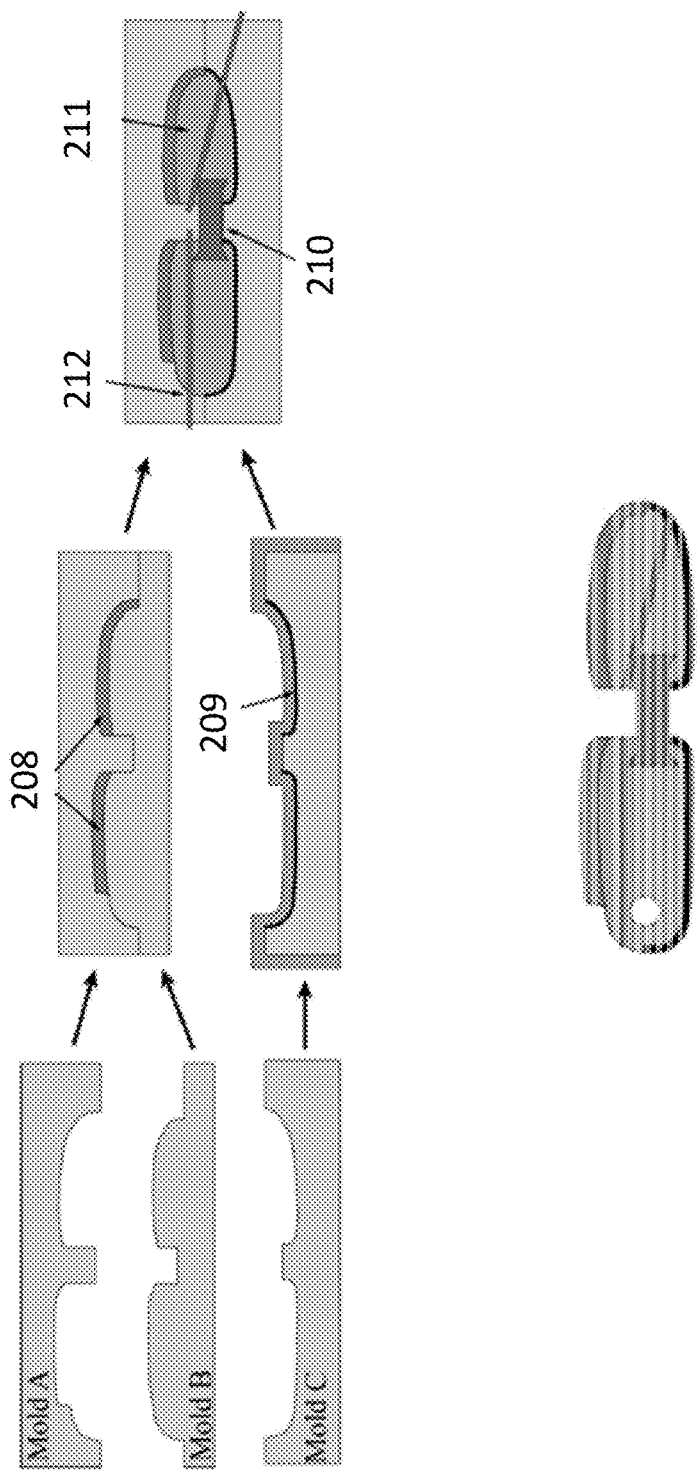
FIG. 29 depicts an illustration of the multi-step manufacturing process for fabricating a composite finger using 3D printed molds.
Figure 32:
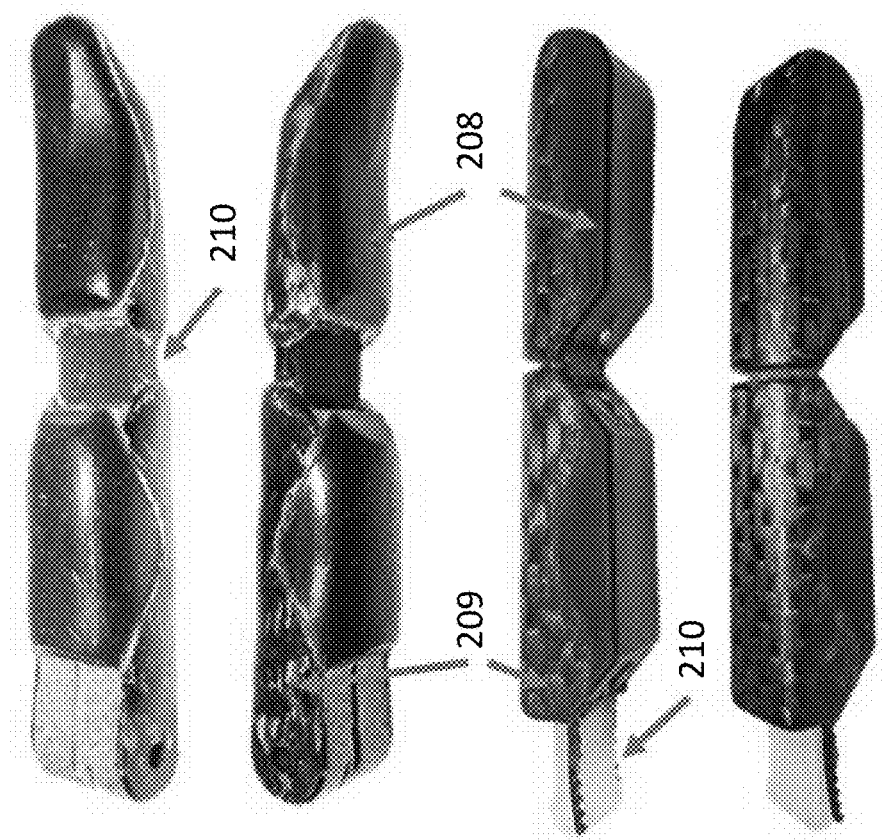
FIG. 32 depicts an image of an example composite finger made from epoxy expanding foam and a carbon-fiber outer shell. The urethane flexure joint connects the distal and proximal digits and the grip pad covers common contact areas.

An exemplary prosthetic hand 200 comprising a double balance bar is depicted in FIG. 1. Referring now to FIG. 2, an exploded view of exemplary prosthetic hand 200 is depicted. Prosthetic hand 200 comprises frame 202, at least one secondary finger unit 204, index finger unit 206, thumb unit 218, and back plate 220. Secondary finger units 204, index finger unit 206, and thumb unit 218 comprise grip pads 208, flexure joints 210, cable guides 212, hinge pins 214, and helical torsion springs 216. Thumb unit 218 is joined to prosthetic hand 200 by thumb block 400. In some embodiments, the finger and thumb units may further comprise a shell 209 (FIG. 29, FIG. 32), such as a carbon fiber shell. In various embodiments, the finger and thumb units are filled with a lightweight material such as a foam 211 (FIG. 29). Prosthetic hand 200 further comprises double balance bar assembly 300 and pulley assembly 500. Prosthetic hand 200 further comprises mounting plate 222 for attachment to other devices.

Prosthetic hand 200 functions as an analog to a natural human hand. Accordingly, frame 202 corresponds to the palm of the natural hand and back plate 220 corresponds to the back of the natural hand. Secondary finger units 204 and index finger unit 206 each comprise a distal piece and a proximal piece, which correspond to the distal phalanges and the proximal phalanges of the respective natural fingers. The distal pieces and the proximal pieces are connected by flexure joints 210, which correspond to the intermediate phalanges of the respective natural fingers. Thumb unit 218 also comprises a distal piece and a proximal piece, which correspond to the distal phalanx and the first metacarpal of the natural thumb. The flexure joint 210 in thumb unit 218 corresponds to the proximal phalanx of the natural thumb.

Each secondary finger unit 204, index finger unit 206, and thumb unit 218 comprises cable guide 212. Cable guide 212 is an elongated member comprising a lumen connecting openings at both ends of cable guide 212, such that a length of string or cable can be passed through cable guide 212.

Flexure joint 210 comprises a flat piece of semi-rigid material. In one embodiment, flexure joint 210 deforms readily upon application of a force, but returns to its original form when the force is released. For example, when the user applies a force, flexure joints 210 bend to allow the prosthetic finger units to close, and when the user releases the force, flexure joints 210 return to their unbent form, thereby straightening the prosthetic finger units. In one embodiment, flexure joint 210 comprises a lateral stabilization structure to limit out of plane bending of flexure joint 210 but still allow necessary out of plane adaptability of the prosthetic finger. In one embodiment, a rigid belt is run parallel to the bending axis of flexure joint 210 on both sides. The belt can bend in plane, but cannot twist or extend, thereby limiting flexure movement in those directions.

Secondary finger units 204 and index finger unit 206 are joined to frame 202 by hinge pins 214. Secondary finger units 204 and index finger unit 206 are able to rotate along hinge pins 214 like the metacarpophalangeal joints in the natural knuckle. Thumb unit 218 is joined to thumb block 400 by hinge pin 214. Thumb unit 218 is able to rotate along hinge pin 214 like the first carpometacarpal joint in the natural hand. In one embodiment, hinge pins 214 are snap pins, such that the pins are easily removable. Ease of removal enables a user to replace broken prosthetic finger units or to exchange prosthetic finger units for specialty finger units at will.

In one embodiment, helical torsion springs 216 are used in conjunction with hinge pins 214 at the prosthetic knuckle. When the user applies a force, helical torsion springs 216 compress to allow the prosthetic finger units to close, and when the user releases the force, helical torsion springs 216 return to their uncompressed form, thereby straightening the prosthetic finger units. In various embodiments, any reversibly deformable mechanism may be used at the prosthetic knuckle. In one embodiment, flexure joints 210 may be used in conjunction with hinge pins 214 at the prosthetic knuckle.

In various embodiments, prosthetic hand 200 comprises features to enhance a user's grip. For example, prosthetic hand 200 may comprise textures, ridges, notches, or any other features that increase friction when grasping or holding an object. In one embodiment, prosthetic hand 200 comprises a plurality of grip pads 208. Grip pads 208 may comprise textures, ridges, notches, or any other features that increase friction when grasping or holding an object. Grip pads 208 may comprise any suitable material, such as rubber or any other polymer. In one embodiment, grip pads 208 comprise two different durometer urethanes for selective deformability in different locations of the gripping surface. For example, areas with a more rigid urethane will be stiffer and more firm while areas filled with a more pliable urethane will be softer.

Figure 4:
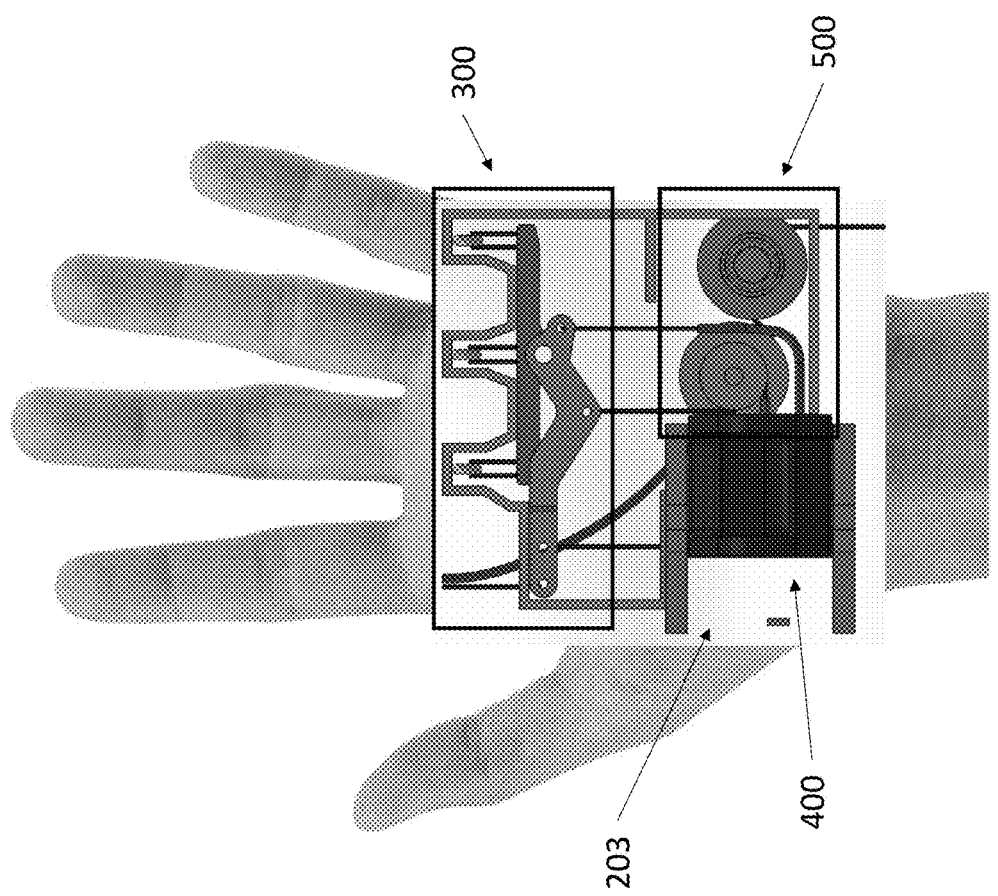
FIG. 4 depicts a schematic of the interior of a double balance bar prosthetic hand overlaid on a hand. The view depicted is the palmar view of a left hand.

Referring now to FIG. 4, a schematic of the interior mechanism of prosthetic hand 200 is overlaid on a hand. FIG. 4 depicts the palmar view of a left hand. FIG. 4 discloses the spatial arrangement of thumb block 400 in thumb block space 203, double balance bar assembly 300, and pulley assembly 500.

Double Balance Bar Assembly

Figure 5:
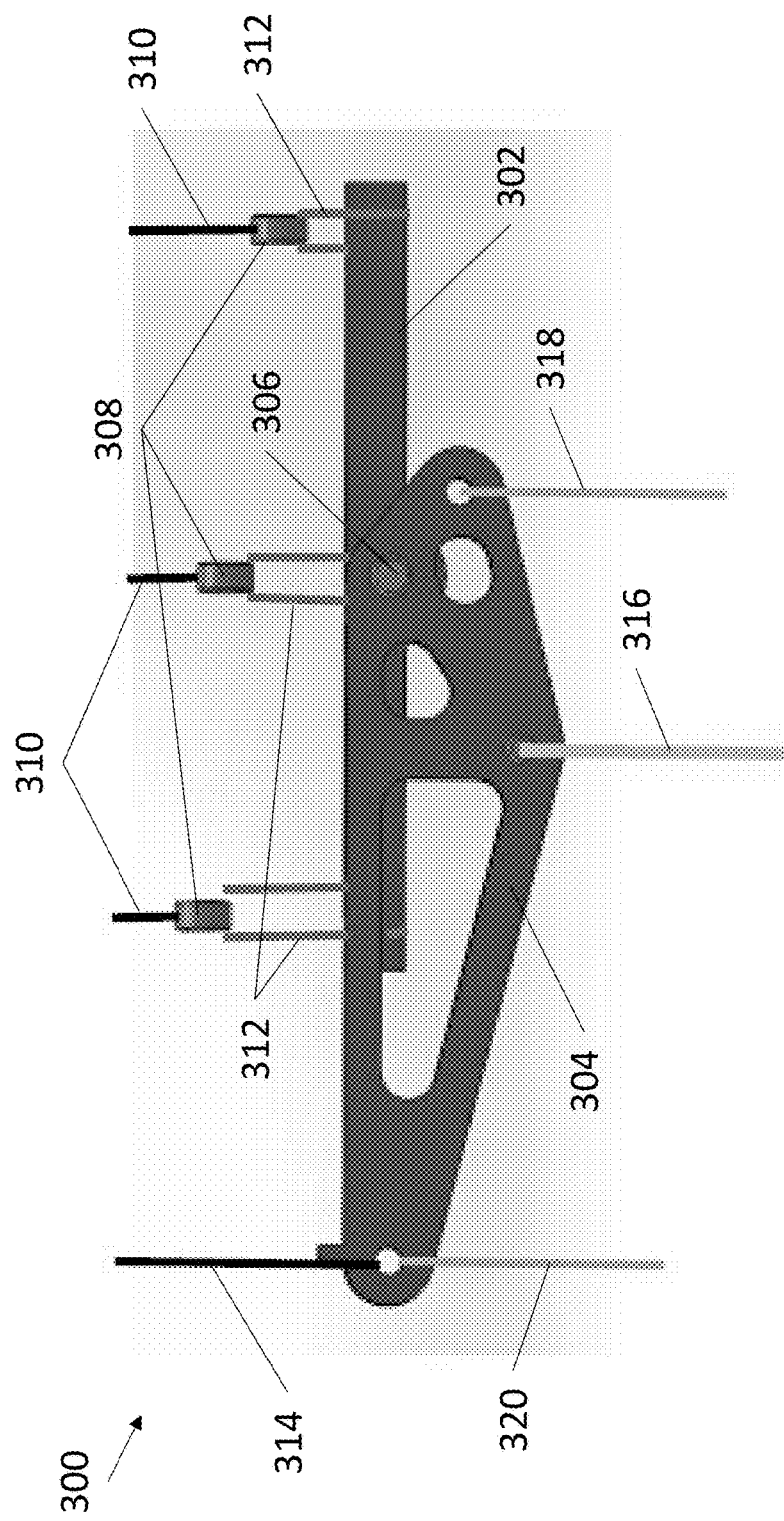
FIG. 5 depicts a schematic of an exemplary double balance bar mechanism.

Referring now to FIG. 5, an exemplary double balance bar assembly 300 is depicted. Double balance bar assembly 300 comprises secondary finger bar 302 and index finger bar 304. Secondary finger bar 302 comprises, at both ends and at its midpoint (corresponding to the locations of the little finger, the ring finger, and the middle finger), a plurality of holes, rods, notches, or any other features through which a string or cable may be threaded through. Secondary finger cable 312 threads through three finger pulleys 308, each of which is connected to an individual finger tendon line 310 to actuate secondary finger units 204.

Index finger bar 304 comprises an attachment point for index finger tendon line 314 and index finger orientation cable 320 at one end, an attachment point for thumb orientation cable 318 at the opposite end, and an attachment point for main actuation cable 316 therebetween. The attachment point for main actuation cable 316 is located on index finger bar 304 at the midpoint of double balance bar assembly 300. Index finger tendon line 314 actuates index finger unit 206.

Secondary finger bar 302 and index finger bar 304 are joined together at pin joint 306. Secondary finger bar 302 comprises pin joint 306 at its midpoint. Index finger bar 304 comprises pin joint 306 at a location between its midpoint and the attachment point for thumb orientation cable 318.

Pulley Assembly and Cabling

Figure 6:
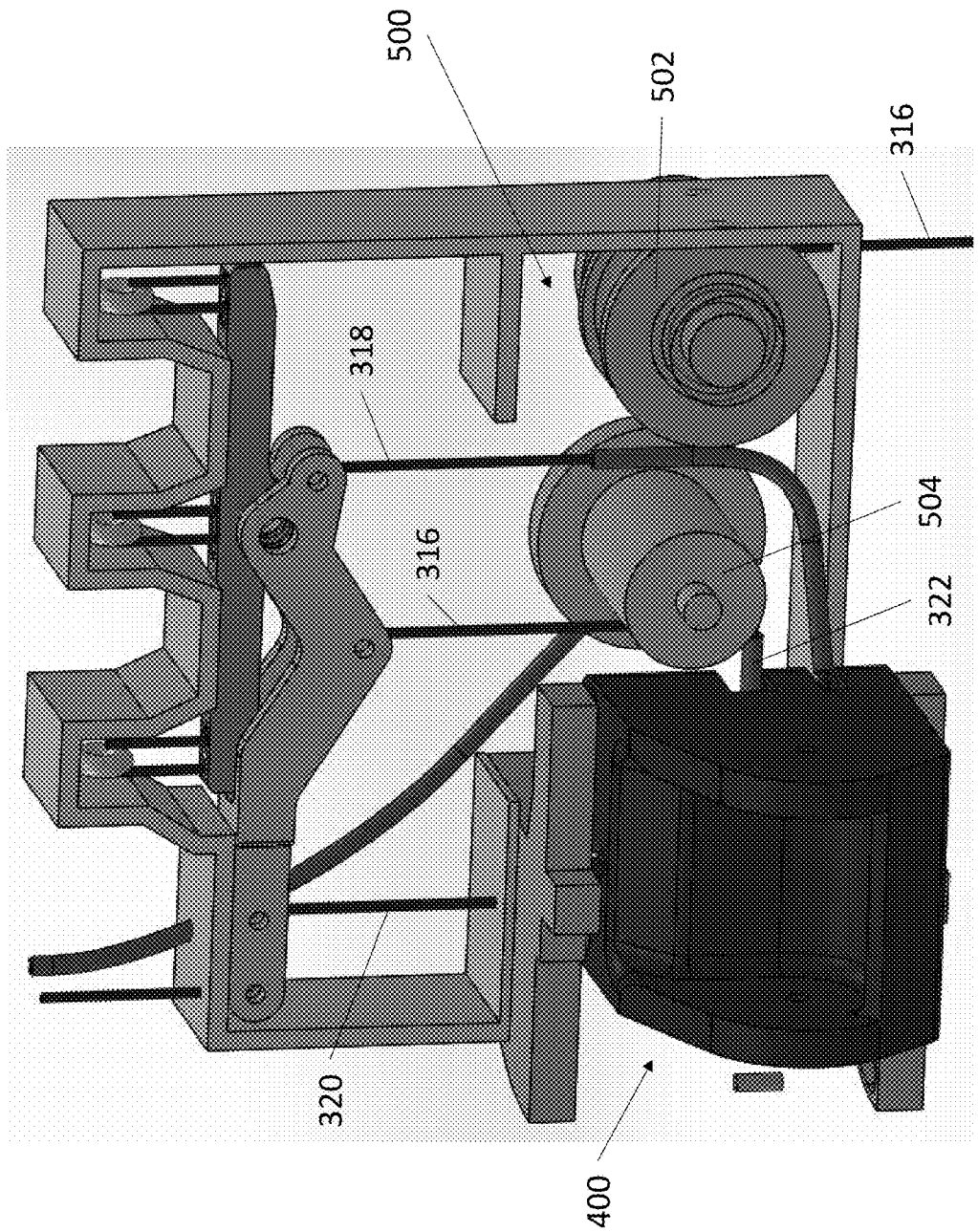
FIG. 6 depicts an isometric view of a schematic of the interior of an exemplary double balance bar prosthetic hand. The view depicted is the palmar view of a left hand.

Referring now to FIG. 6, an exemplary pulley assembly 500 is depicted. Pulley assembly 500 comprises first pulley 502 and second pulley 504. Main actuation cable 316 extends proximally from index finger bar 304, loops proximally underneath second pulley 504, loops distally over first pulley 502, and exits prosthetic hand 200 proximally.

Thumb orientation cable 318 extends proximally from index finger bar 304, loops underneath second pulley 504, and is anchored to thumb block 400 within.

Thumb tendon line 322 is attached to second pulley 504 at one end, extends through thumb block 400, and terminates in thumb unit 218 to actuate thumb unit 218.

Index finger orientation cable 320 extends proximally through thumb block space 203 (FIG. 7) and is anchored to the proximal end of index finger cable guide 434 (FIG. 7, FIG. 9, FIG. 13, FIG. 16, FIG. 19)

Thumb Block

Figure 7:
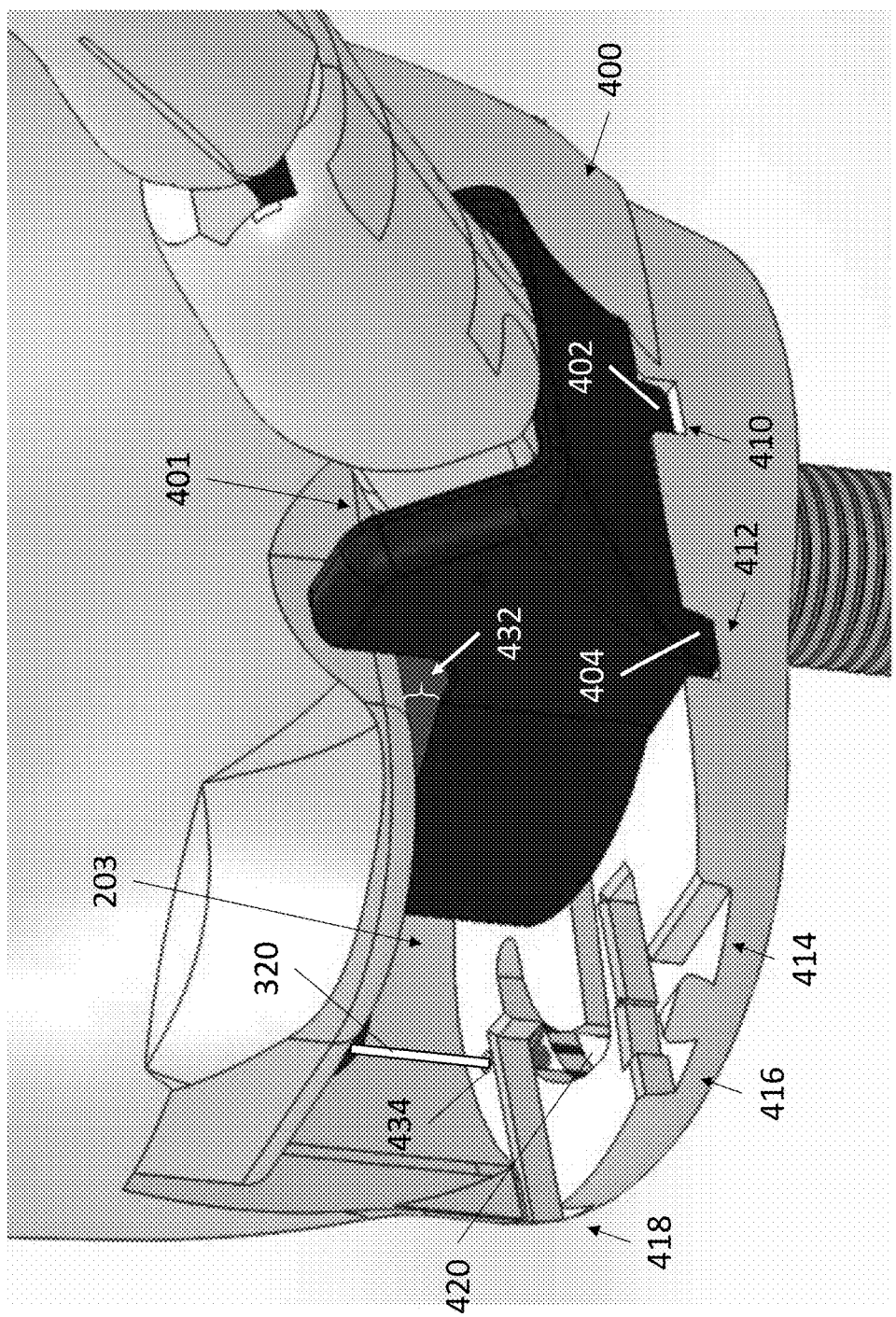
FIG. 7 depicts an isometric view of the thumb locking mechanism. The hand depicted is a left hand.

Referring now to FIG. 7, an exemplary thumb block 400 and thumb block space 203 is depicted. Thumb block 400 comprises thumb slot 401 for attachment of thumb unit 218. Thumb block 400 further comprises first tab 402 and second tab 404. Thumb block 400 and thumb slot 203 are dimensioned such that the difference in height between the two leaves room for gap 432. Gap 432 comprises a height that is at least equal to the heights of first tab 402 and second tab 404. Thumb block 400 further comprises first pin 406 and second pin 408 (visible in FIG. 8).

Figure 8:
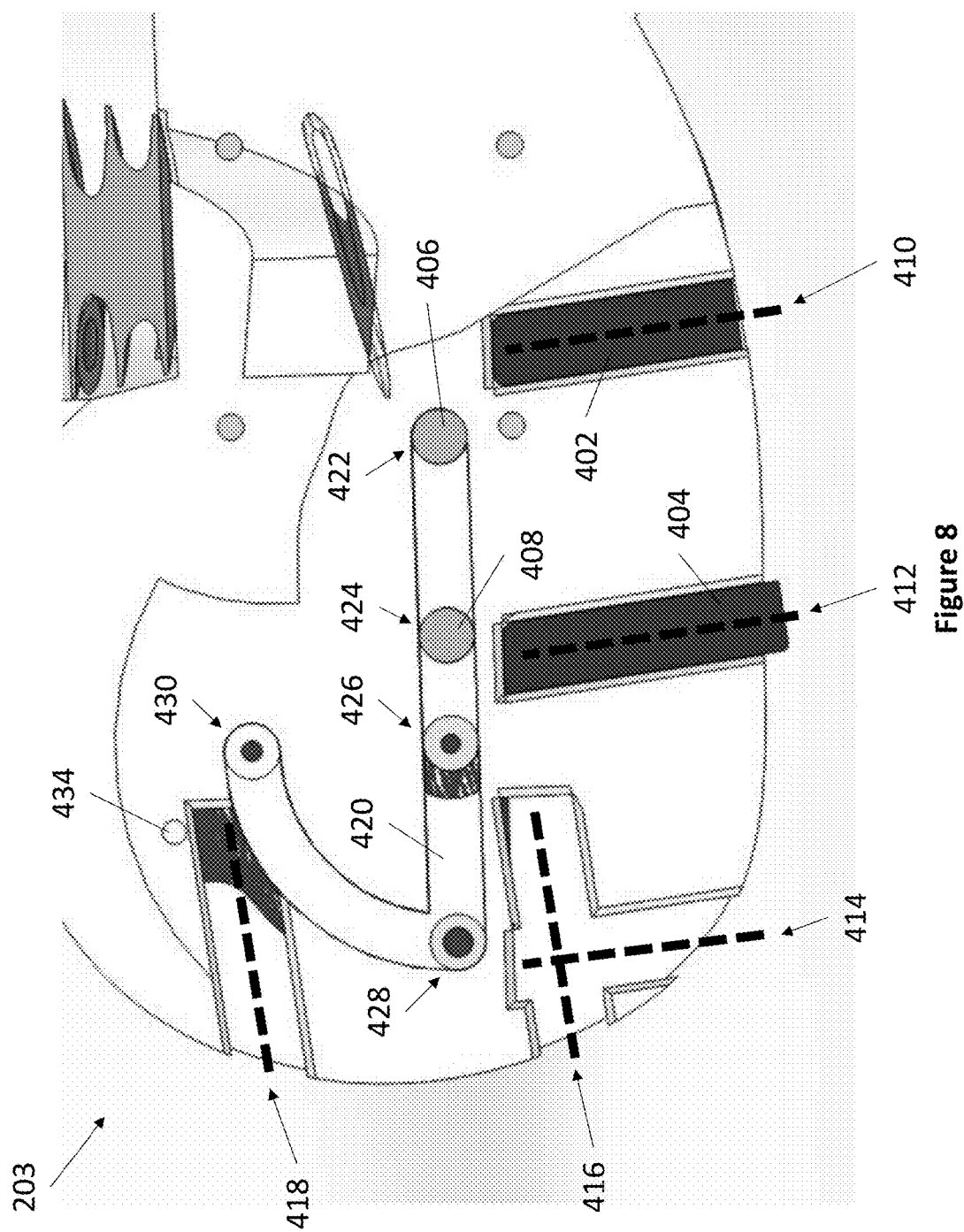
FIG. 8 depicts a top down view of a cross section of the thumb mechanism of the double balance bar prosthetic hand. The hand depicted is a left hand.
Figure 9:
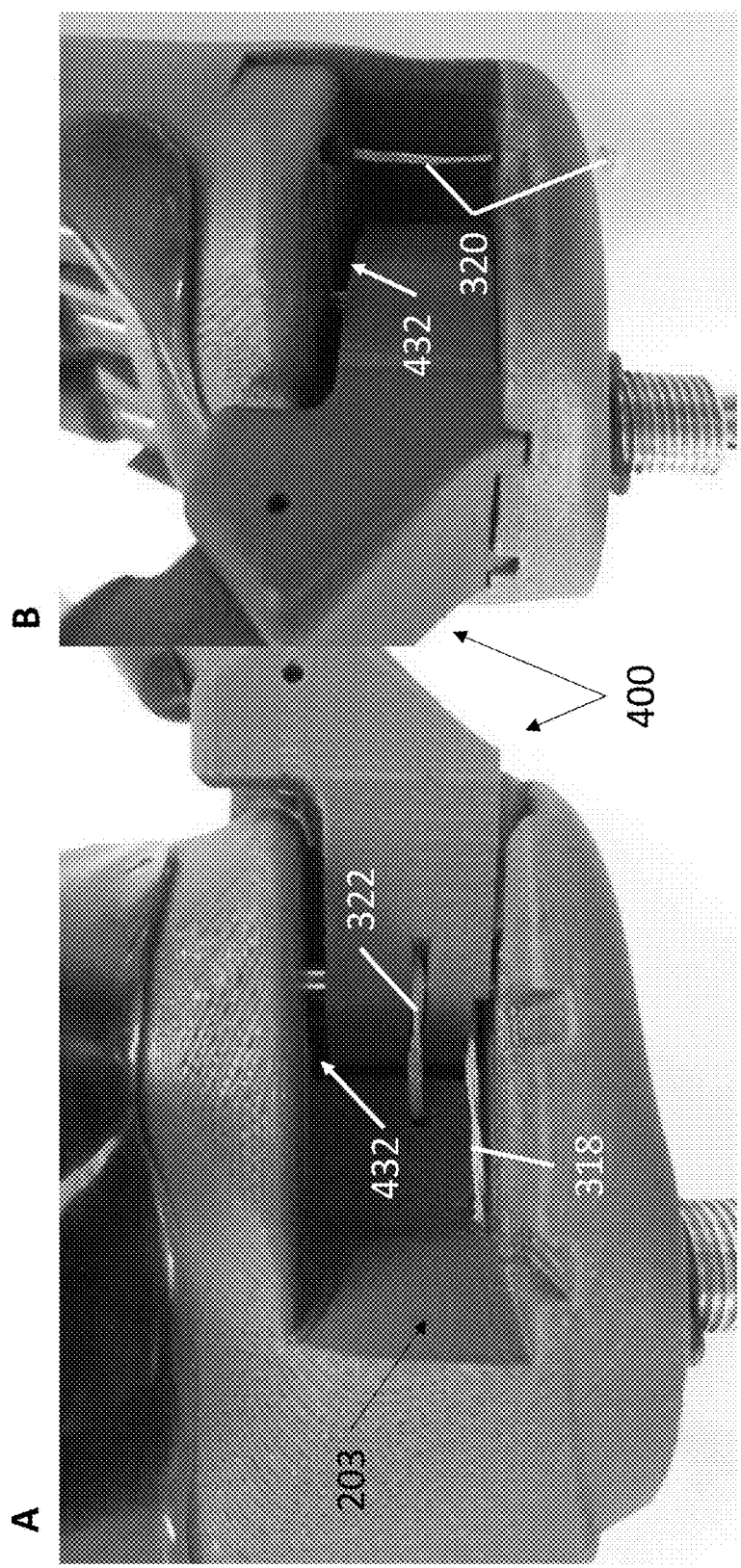
FIG. 9 depicts the thumb mechanism of an exemplary double balance bar prosthetic hand. The hand depicted is a right hand.

Thumb block space 203 comprises a series of tab slots and pin slots for securing thumb block 400 in various positions. Referring now to FIG. 8, a cutaway top down view of thumb block space 203 is depicted. Thumb block space 203 comprises first tab slot 410, second tab slot 412, third tab slot 414, fourth tab slot 416, and fifth tab slot 418, wherein the dashed lines represent the orientation of first tab 402 and second tab 404 when inserted into the plurality of tab slots. First tab 402 and second tab 404 fit in the plurality of tab slots to lock thumb block 400 into place. Thumb block space 203 further comprises pin track 420, along which defines the possible range of movement for first pin 406 and second pin 408. Pin track 420 comprises first pin slot 422, second pin slot 424, third pin slot 426, fourth pin slot 428, and fifth pin slot 430. First pin 406 and second pin 408 fit in the plurality of pin slots to lock thumb block 400 into place.

Thumb Configuration and Grasp Type

Prosthetic hand 200 comprises a plurality of thumb block configurations switchable by the user that correspond to three grasp types. Thumb unit 218 acts as a lever to change the grasp type by moving thumb block 400 along the internal path within thumb block space 203, as described elsewhere herein. Thumb block 400 locks into place when in the correct grasp position to prevent unwanted movement in thumb block 400.

In one embodiment, the grasp types comprise a power grasp, a precision grasp, and a lateral grasp. The power grasp provides a fully adaptive grasp of the thumb unit and all four finger units. The precision grasp provides a symmetric grasp between the index finger unit and thumb unit only and closes the secondary finger units. The lateral grasp fixes the four finger units in a closed position for hooking around an object, and the thumb unit grasps to pinch the side surface of the prosthetic hand.

Figure 3:
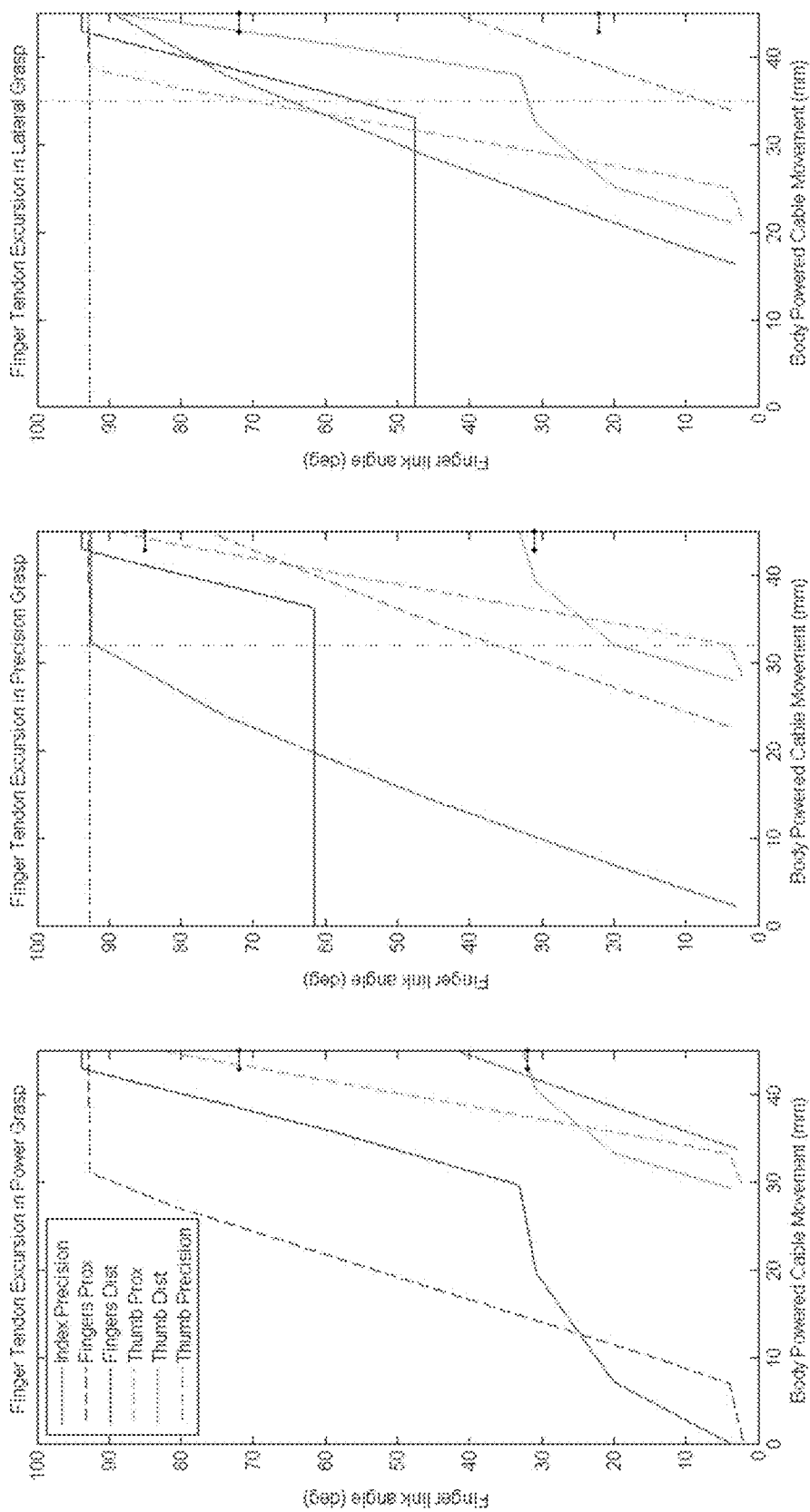
FIG. 3 is a series of graphs depicting the results of mapping finger movement to main actuator cable movement. The pattern of cable motion for each finger was optimized to allow for proper closure timing in all three grasps by simply adjusting the slack added or subtracted from each finger when the thumb is moved. The amount of movement of the differential mechanism was also adjusted to allow for ideal closing patterns over the three grasp types

In various embodiments, the length or the amount of slack in the cables and tendon lines are tuned to optimize finger unit movement. Referring now to FIG. 3, an example of finger movement mapping optimization is depicted. The pattern of cable motion for each finger unit was optimized for proper closure timing in the three grasp types by adjusting the slack added or subtracted from each finger unit when thumb block 400 was moved. The amount of movement of the double balance bar assembly 300 was adjusted to allow for ideal closing patterns over the three grasp types.

Power Grasp Configuration

Figure 10:
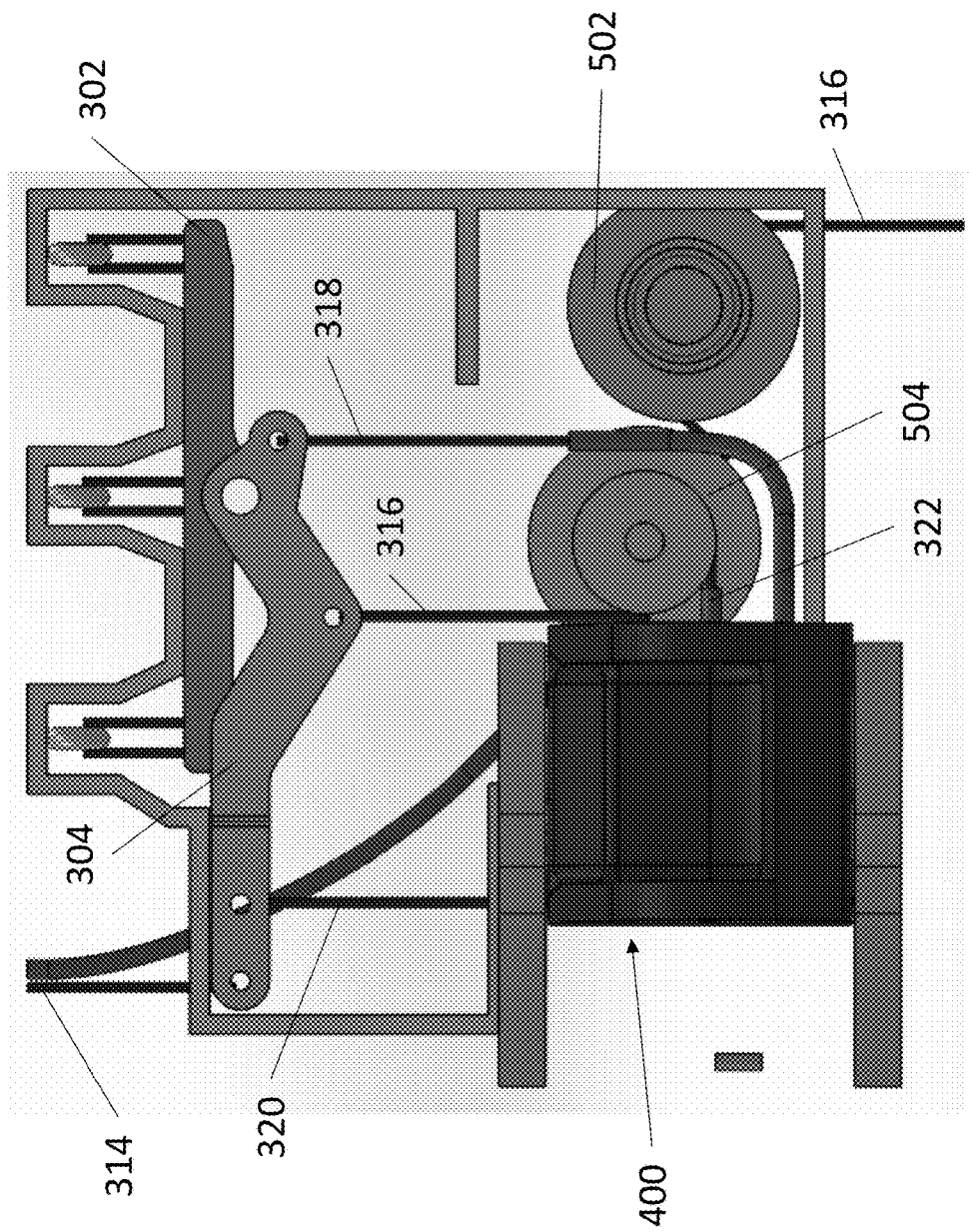
FIG. 10 depicts a schematic of the interior of an exemplary double balance bar prosthetic hand in a power grasp configuration. The view depicted is the palmar view of a left hand.
Figure 11:
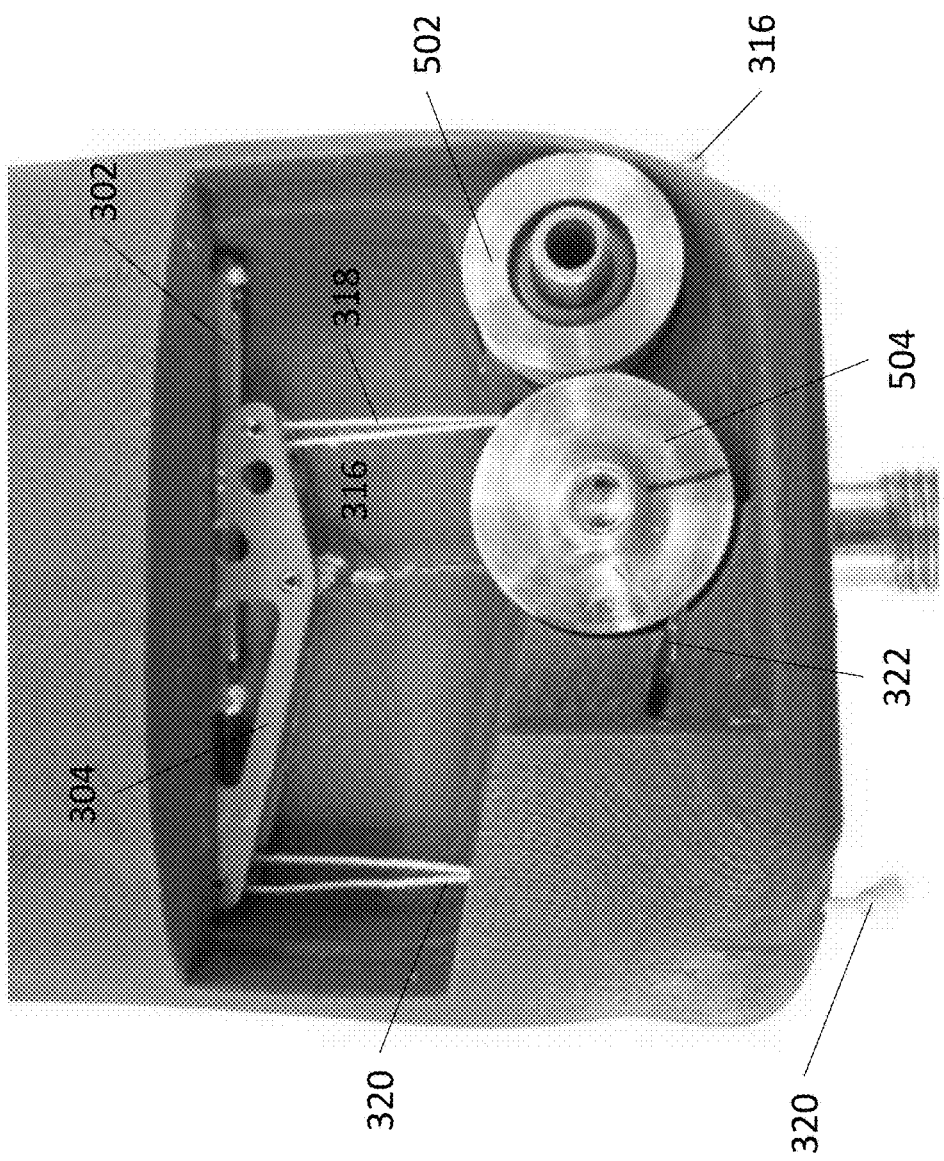
FIG. 11 depicts an exemplary double balance bar prosthetic hand in a power grasp configuration. The back plate has been removed to expose the double balance bar mechanism. The view depicted is the dorsal view of a right hand.
Figure 12:
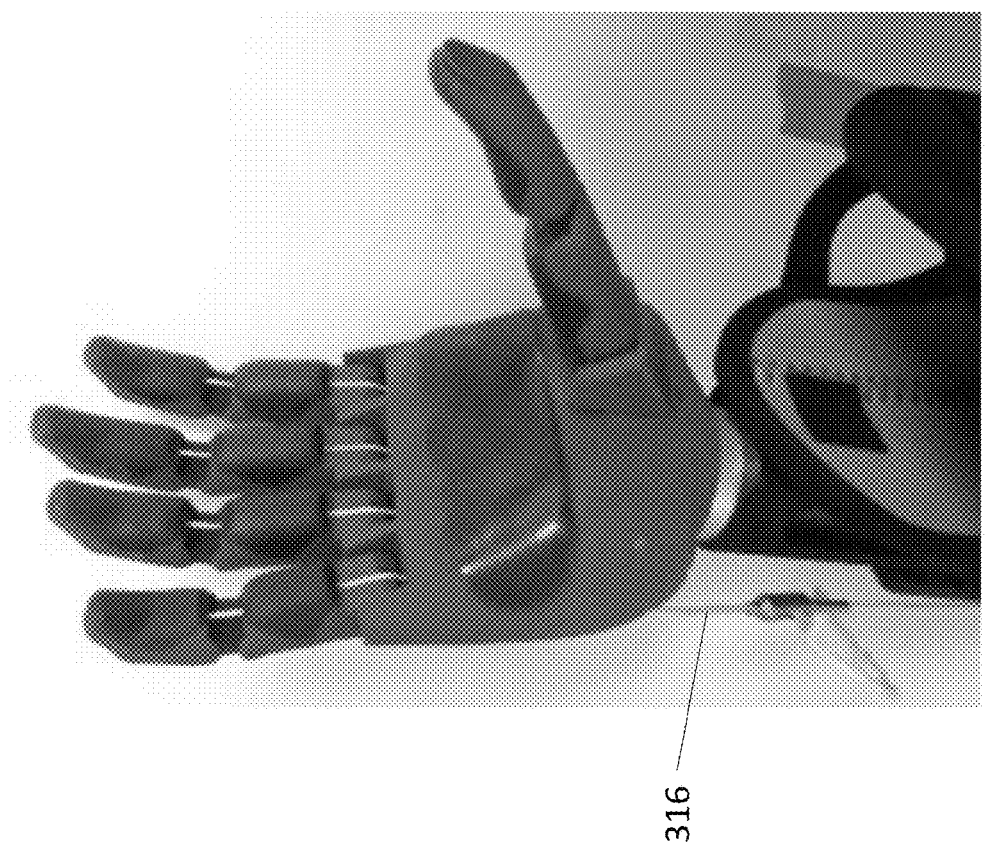
FIG. 12 depicts an exemplary double balance bar prosthetic hand in a power grasp configuration. The thumb is shown aligned with the middle finger. The hand depicted is a right hand.
Figure 13:
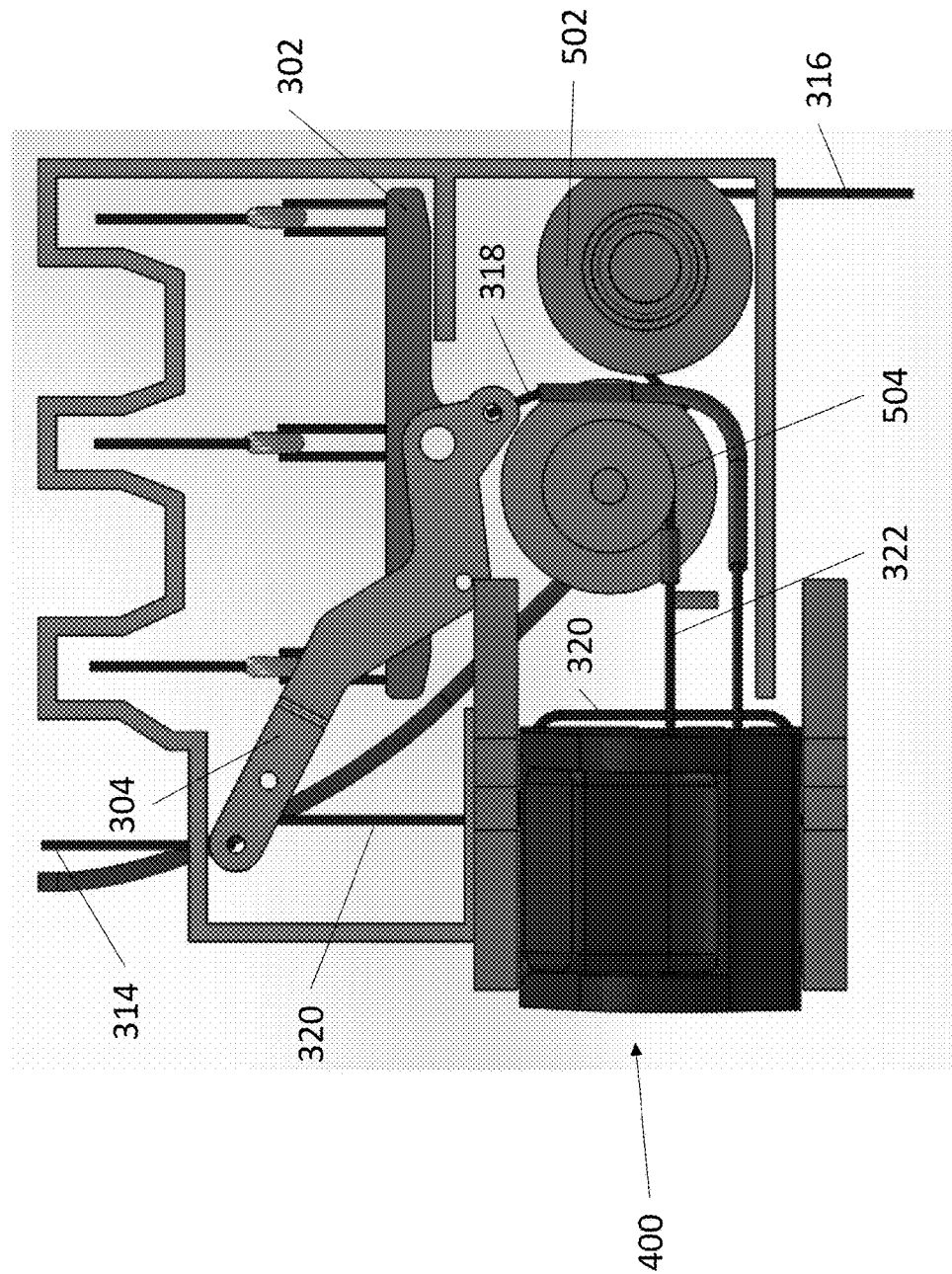
FIG. 13 depicts a schematic of the interior of an exemplary double balance bar prosthetic hand in a precision grasp configuration. The view depicted is the palmar view of a left hand.
Figure 14:
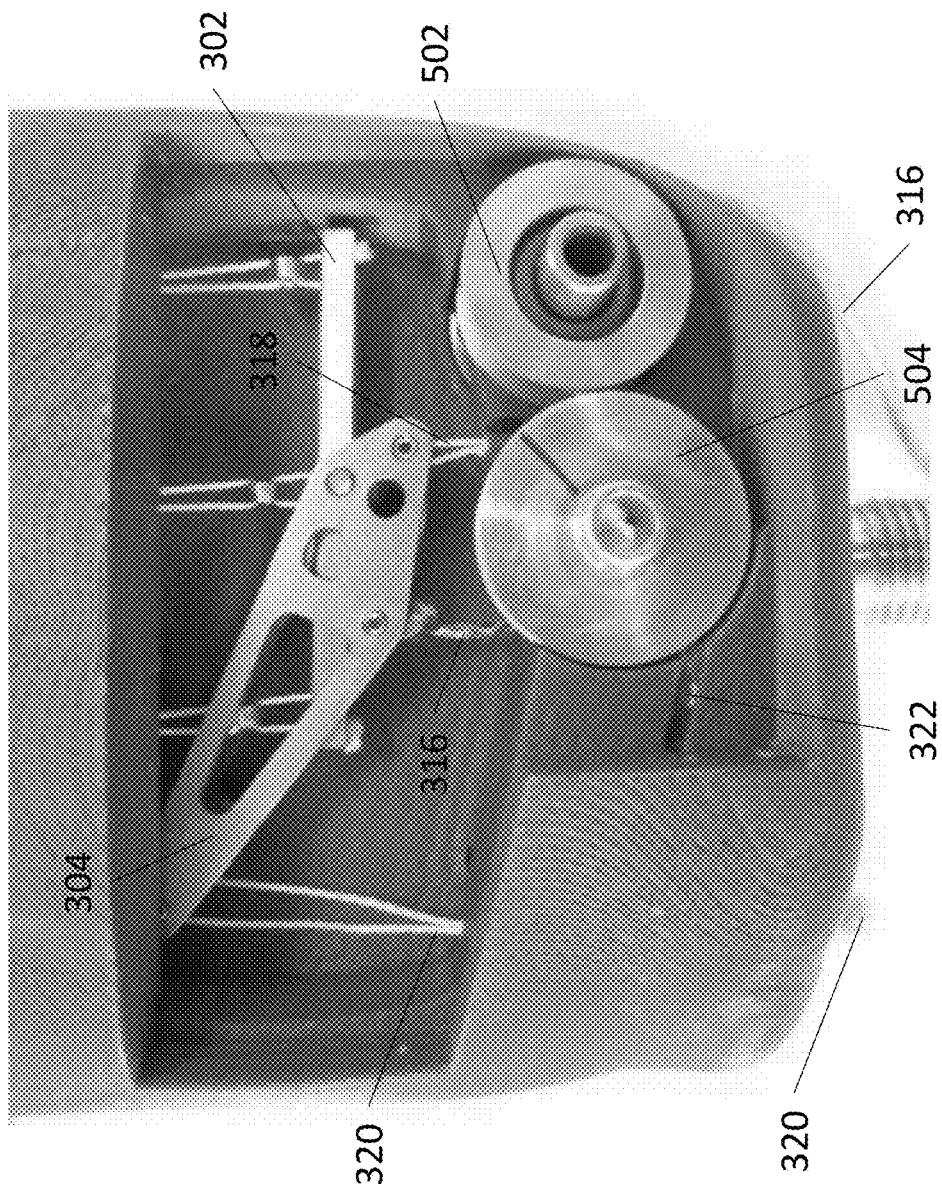
FIG. 14 depicts an exemplary double balance bar prosthetic hand in a precision grasp configuration. The back plate has been removed to expose the double balance bar mechanism. The view depicted is the dorsal view of a right hand.
Figure 15:
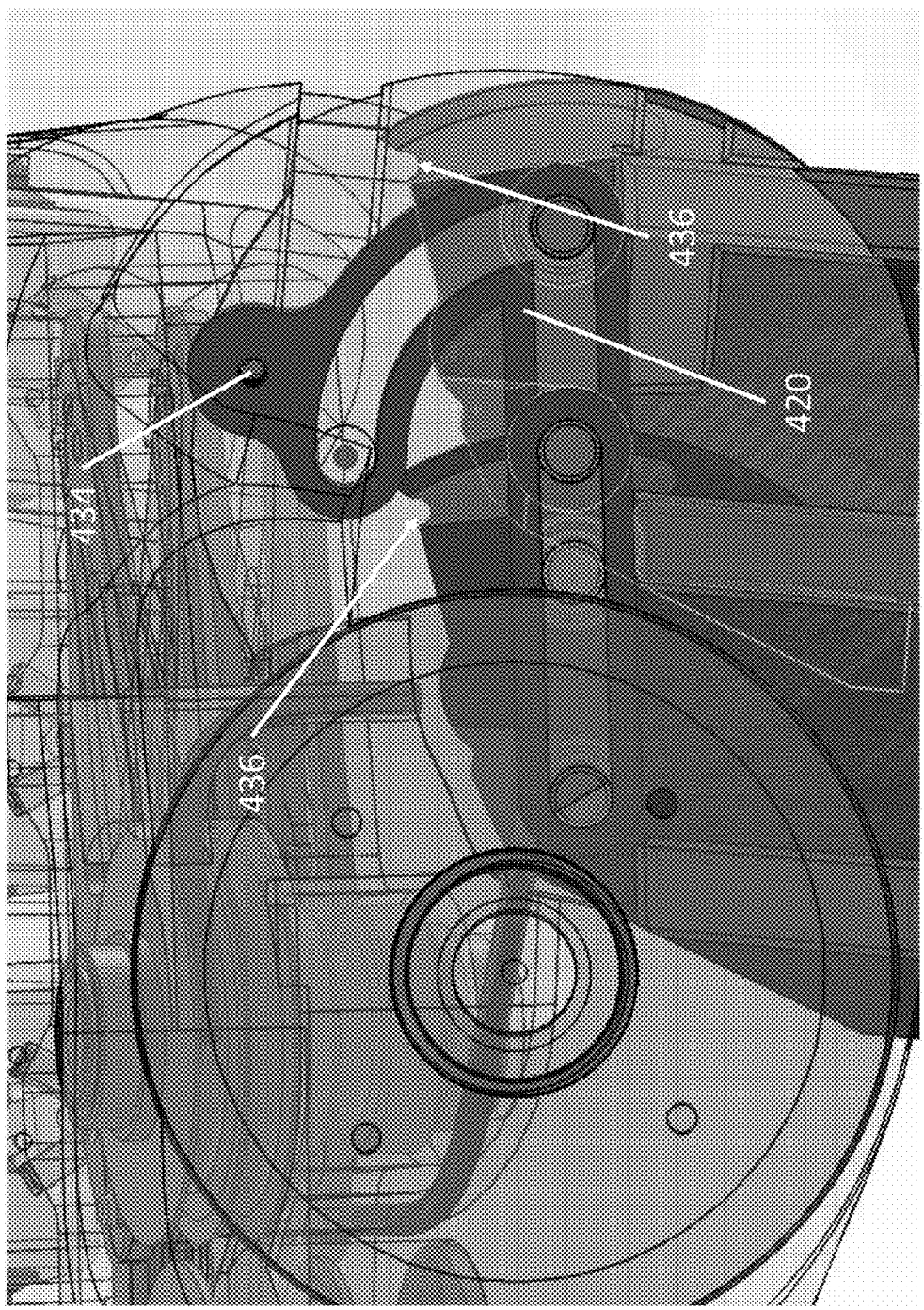
FIG. 15 depicts an x-ray view of the thumb mechanism from the bottom. The thumb block is shown in the power grasp configuration and the precision grasp configuration. The hand depicted is a left hand.
Figure 16:
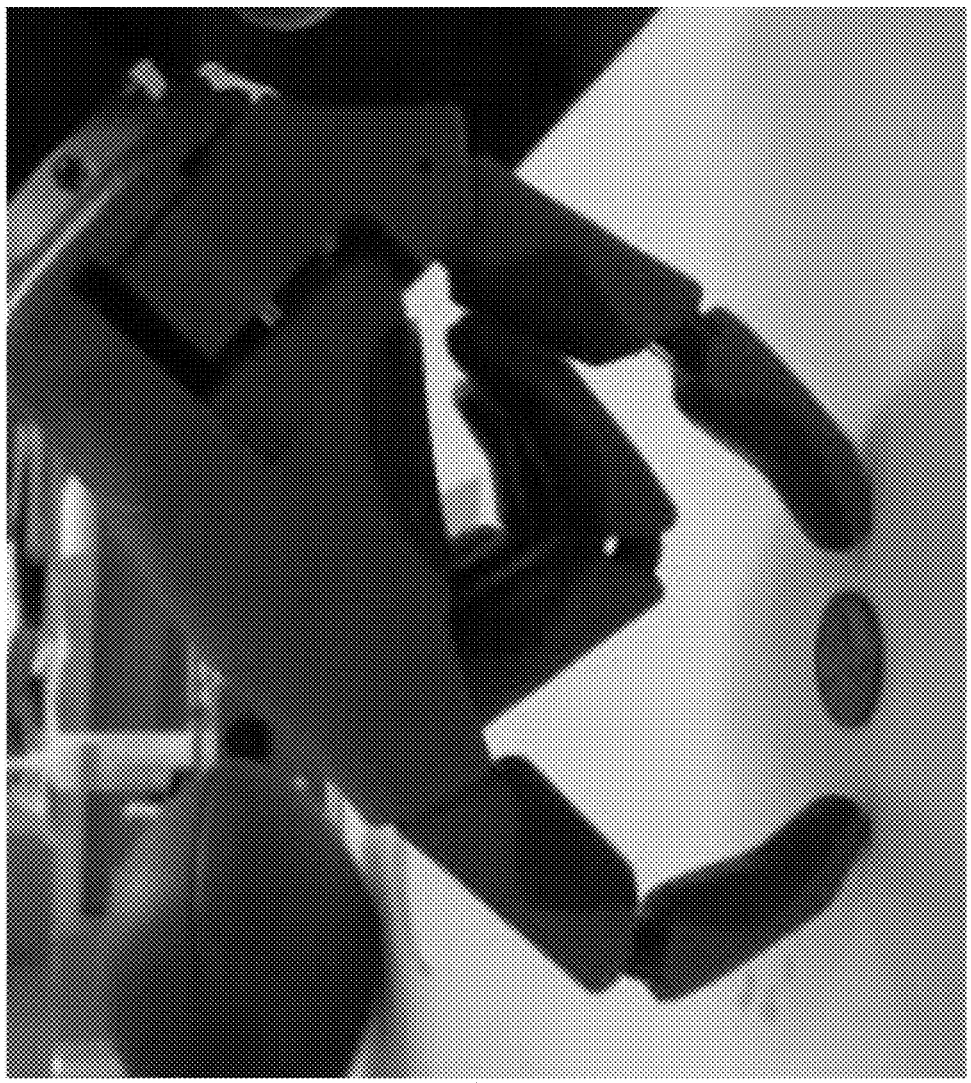
FIG. 16 depicts an exemplary double balance bar prosthetic hand in a precision grasp configuration. The thumb is shown aligned with the index finger. The hand depicted is a right hand.

Referring now to FIG. 10, FIG. 11, and FIG. 12, various images of prosthetic hand 200 in a power grasp configuration are depicted. All four finger units are fully open, and thumb unit 218 is aligned with the middle secondary finger unit. In this configuration, thumb block 400 is positioned such that first tab 402 is seated in first tab slot 410, second tab 404 is seated in second tab slot 412, first pin 406 is seated in first pin slot 422, and second pin 408 is seated in second pin slot 424.

Double balance bar assembly 300 is in a raised position, and both secondary finger bar 302 and index finger bar 304 are parallel to each other. When main actuation cable 316 is pulled, double balance bar assembly 300 is pulled proximally, which in turn pulls finger tendon lines 310 and index finger tendon line 314 proximally at an equal distance to close all four finger units. When main actuation cable 316 is pulled, the rotation of second pulley 504 pulls thumb tendon line 322 and closes thumb unit 218.

Precision Grasp Configuration

Referring now to FIG. 13, FIG. 14, FIG. 15, and FIG. 16, various images of prosthetic hand 200 in a precision grasp configuration are depicted. The secondary finger units are closed, and thumb unit 218 is aligned with index finger unit 206.

To shift prosthetic hand 200 into the precision grasp configuration, e.g. from the power grasp configuration, thumb block 400 is lifted distally into the space of gap 432 to unseat first tab 402, second tab 404, first pin 406, and second pin 408. Thumb block 400 is then pushed laterally and released such that first tab 402 is seated in second tab slot 412, second tab 404 is seated in third tab slot 414, first pin 406 is seated in third pin slot 426, and second pin 408 is seated in fourth pin slot 428.

Placing thumb block 400 in the precision grasp configuration applies tension on thumb orientation cable 318, which pulls double balance bar assembly proximally. Since tension is only present from thumb orientation cable 318, only secondary finger bar 302 is in a lowered position, which pulls secondary finger units 204 into a closed position. Index finger bar 304 is partially pulled proximally due to its attachment to secondary finger bar 302 at pin joint 306, but the end attached to index finger tendon line 314 remains in a raised position.

When main actuation cable 316 is pulled, index finger bar 304 is fully pulled proximally, which in turn pulls index finger tendon line 314 to close index finger unit 206. When main actuation cable 316 is pulled, the rotation of second pulley 504 pulls thumb tendon line 322 and closes thumb unit 218. Since thumb unit 218 and index finger unit 206 are in alignment in the precision grasp configuration, pulling main actuation cable 316 causes the tips of index finger unit 206 and thumb unit 218 to meet and the user is able to pick up items with precision.

Lateral Grasp Configuration

Figure 17:
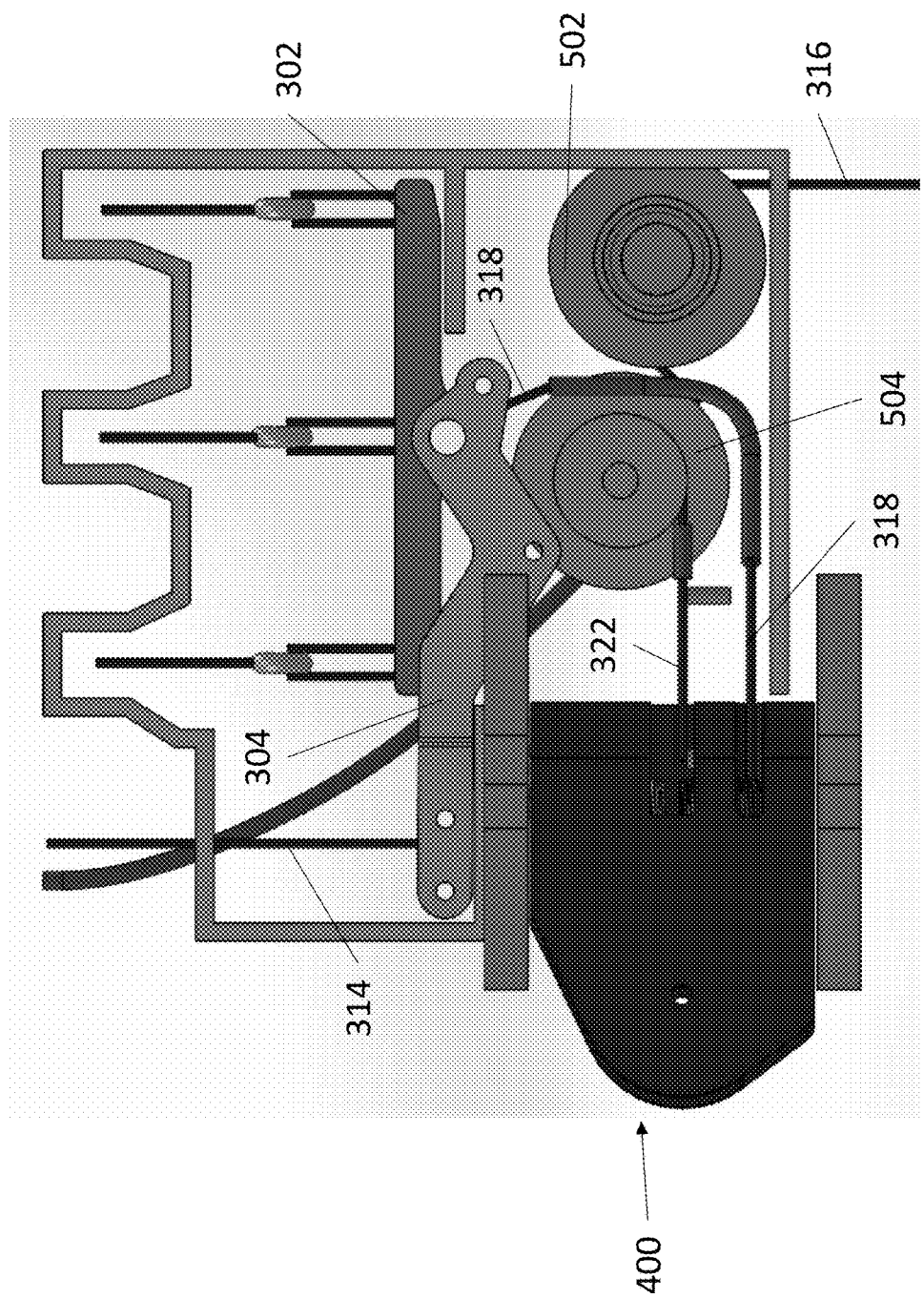
FIG. 17 depicts a schematic of the interior of an exemplary double balance bar prosthetic hand in a lateral grasp configuration. The view depicted is the palmar view of a left hand.
Figure 18:
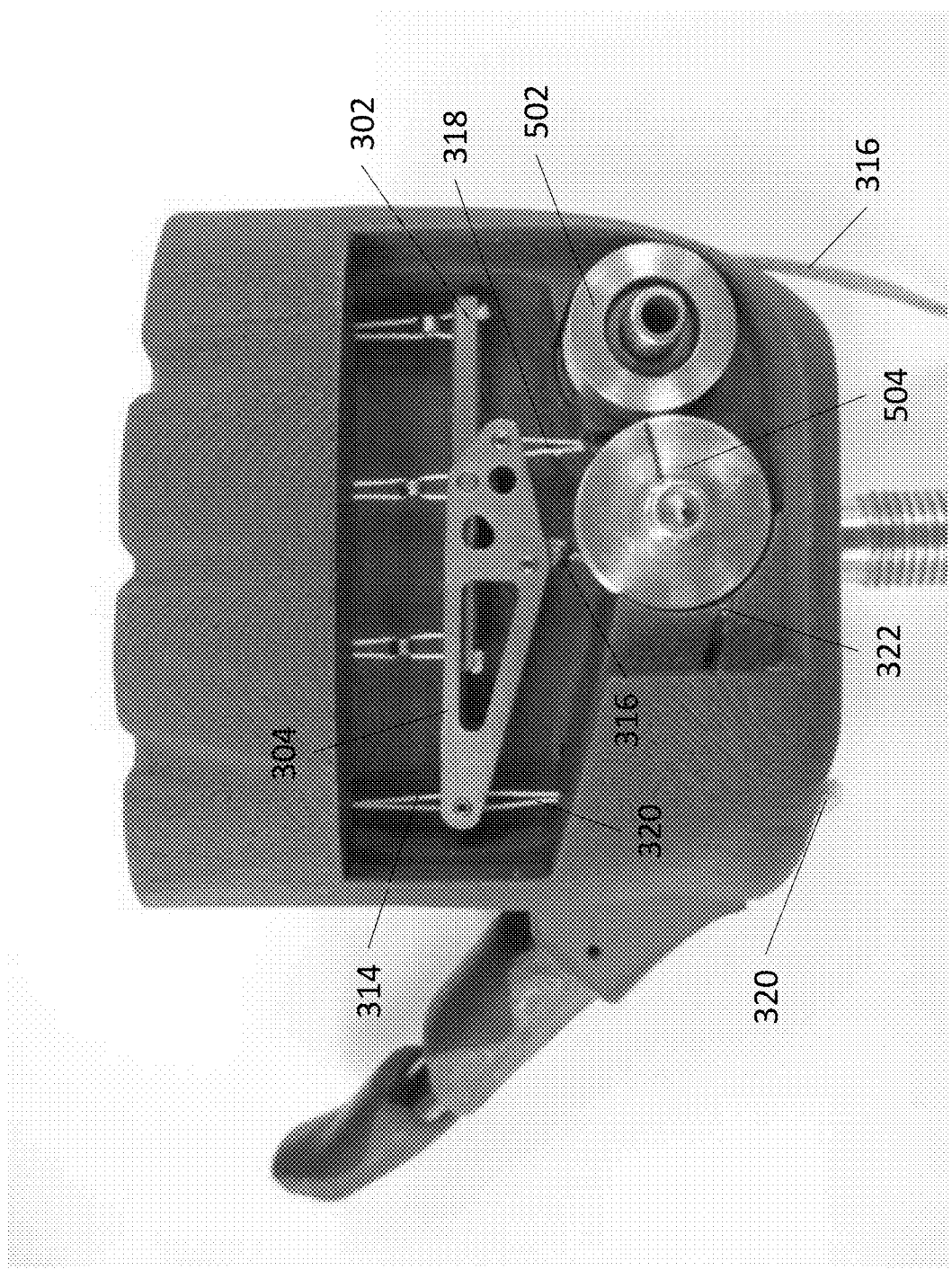
FIG. 18 depicts an exemplary double balance bar prosthetic hand in a lateral grasp configuration. The back plate has been removed to expose the double balance bar mechanism. The thumb is shown extending from the side of the hand. The view depicted is the dorsal view of a right hand.
Figure 19:
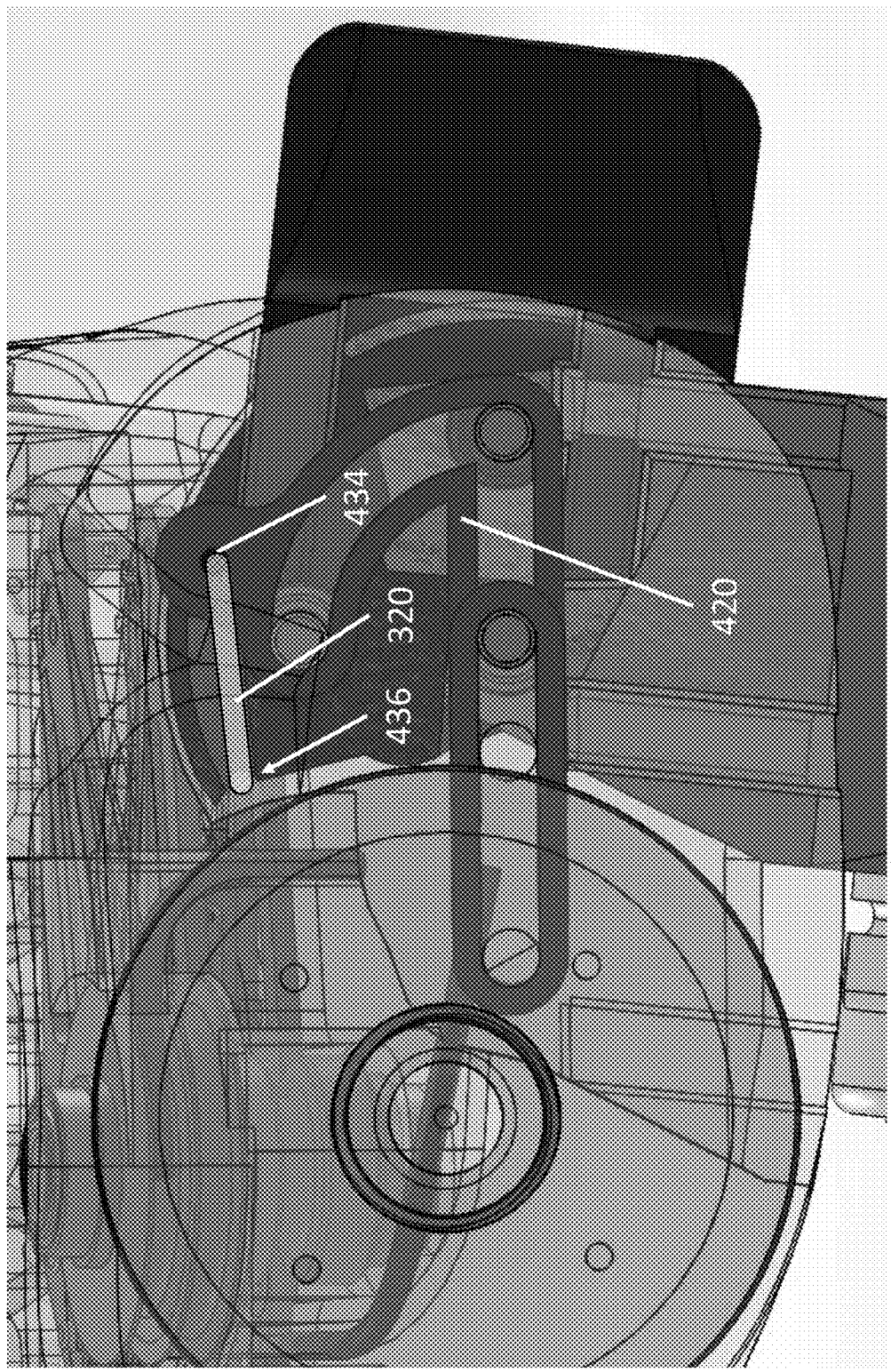
FIG. 19 depicts an x-ray view of the thumb mechanism from the bottom. The thumb block is shown in the precision grasp configuration and the lateral grasp configuration. The hand depicted is a left hand.

Referring now to FIG. 17, FIG. 18, and FIG. 19, various images of prosthetic hand 200 in a lateral grasp configuration are depicted. The four finger units are closed, and thumb unit 218 is positioned to the side of prosthetic hand 200.

To shift prosthetic hand 200 into the lateral grasp configuration, e.g. from the precision grasp configuration, thumb block 400 is lifted distally into the space of gap 432 to unseat first tab 402, second tab 404, first pin 406, and second pin 408. Thumb block 400 is then rotated and released such that first tab 402 is seated in fourth tab slot 416, second tab 404 is seated in fifth tab slot 418, first pin 406 is seated in third pin slot 426, and second pin 408 is seated in fifth pin slot 430

Placing thumb block 400 in the lateral grasp configuration applies tension on thumb orientation cable 318, which pulls double balance bar assembly proximally. Since tension is present from thumb orientation cable 318, secondary finger bar 302 is in a lowered position, which pulls secondary finger units 204 into a closed position.

Placing thumb block 400 in the lateral grasp configuration further applies tension on index finger orientation cable 320. Visible in FIG. 15 and FIG. 19, thumb block 400 comprises index finger cable catch 436. As thumb block 400 is rotated into the lateral grasp configuration, index finger cable catch 436 hooks onto index finger orientation cable 320 and applies tension onto index finger orientation cable 320. This action pulls index finger bar 304 proximally, bringing index finger bar 304 into a fully lowered position parallel to secondary finger bar 302 and pulling index finger unit 206 into a closed position.

When main actuation cable 316 is pulled, no movement occurs in all four finger units because they are already in the closed position. When main actuation cable 316 is pulled, the rotation of second pulley 504 pulls thumb tendon line 322 and closes thumb unit 218. Since thumb unit 218 is positioned to the side of prosthetic hand 200, pulling main actuation cable 316 causes thumb unit 218 to close against the side of prosthetic hand 200.

Applications of the Prosthetic Hand

The prosthetic hand of the present invention greatly improves grasping performance and allows the hand to perform three distinct grasping behaviors. In various embodiments, prosthetic hand 200 may be used as a prosthetic terminal device, for example, in a body-powered harness such that a user may control the device with shoulder movements. The device is also amenable for use in myoelectric prostheses. The device is suitable for users having transradial or transhumeral amputations.

In another embodiment, the mechanism of the prosthetic hand may be used in robotics. For example, the prosthetic hand may be used in humanoid robots for better replication of hand function. In another embodiment, the prosthetic hand may be used in a commercial or supply line setting. For example, the grasping mechanism of the present invention may be used for gripping objects having obscure shapes off supply lines for inspection or sorting. It may also be used as manipulators in environments that are unsuitable for human workers, such as space or high radiation areas.

Grasp Locking Mechanism

Figure 20:
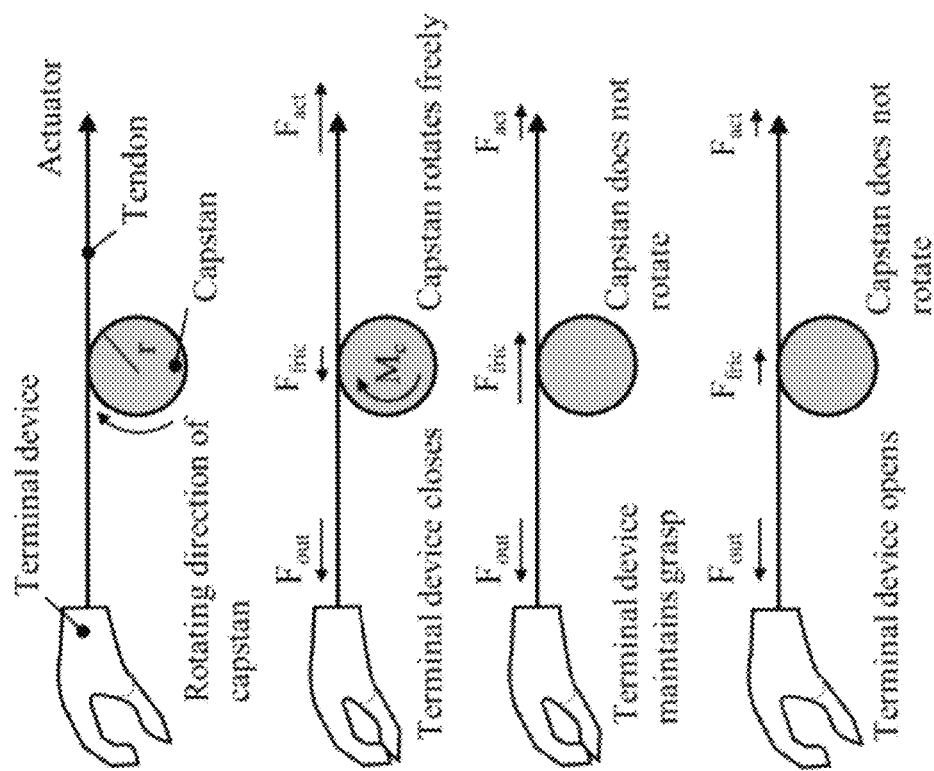
FIG. 20 depicts an exemplary passive capstan-based grasp enhancement feature to help users maintain a higher grip force on objects while reducing fatigue.

The present invention also provides a locking feature to help users maintain a higher grip force on objects while reducing fatigue. In one embodiment, a unidirectional rotating surface is used as a means for users to be able to grasp an object and to be able to hold said object with a minimal input force. Referring now to FIG. 20, an exemplary embodiment of a grasp locking mechanism is depicted, wherein the terminal device is the prosthetic hand of the present invention, and the actuator input cable is connected to the main actuation cable of the prosthetic hand. The grasp locking mechanism is external from the prosthetic hand and may form part of, for example, a body-powered harness.

In one embodiment, the grasp locking mechanism wraps the actuator input cable around the unidirectional rotating surface and uses friction to hold a grasp in place until the shoulder controlling the body-powered harness is completely relaxed. This will help to reduce fatigue for users as well as make it easier to hold and move objects. In one embodiment, the surface of the locking mechanism incorporates two features which allow the mechanism to hold the input cable in place (locked) while also preventing the cable from wrapping over itself, which would cause the cable to tangle and permanently lock the position of the cable and hand. The first feature comprises a textured surface to the unidirectional rotating surface to provide the correct amount of friction between the locking mechanism surface and input cable, which allows the user to hold an object after grasping with less force exerted by the input arm. For example, the first feature may be sand-blasted aluminum. The second feature comprises cable guides to prevent any tangling in the input cable that is wrapped around the locking mechanism. For example, a specific surface geometry that guides the input cable as it moves along the surface of the locking mechanism may be used. The surface geometry may incorporate a fillet and raised edge on each side so that the input cable will move up this fillet as a ramp while the mechanism rotates.

Method of Manufacture

Prosthetic hand 200 may be made using any suitable method. For example, prosthetic hand 200 may be made using methods including, but not limited to: 3D printing, machining, molding, casting, and the like. Prosthetic hand 200 may be made from any suitable material. For example, prosthetic hand 200 may be made from materials including, but not limited to: polylactic acid (PLA), acrylonitrile butadiene styrene (ABS), foam, carbon fiber, aluminum, wood, and the like.

In one embodiment, prosthetic hand 200 is made using an additive manufacturing method of the present invention. The additive manufacturing method is useful for fabricating frame 202, back plate 220, as well as the components of secondary finger units 204, index finger unit 206, and thumb unit 218.

The additive manufacturing method layers molded carbon-fiber shells with epoxy expanded foam and integrates features such as flexible joints and variable stiffness grip surfaces. For example, in the manufacturing of a prosthetic finger, the method produces a prosthetic finger having three main layers: the carbon-fiber structural shell located on the back and sides of the finger, a lightweight foam filler material that serves to bond the internal components together, and a soft urethane grip surface that mates seamlessly with the shape of the structural shell.

Figure 28:
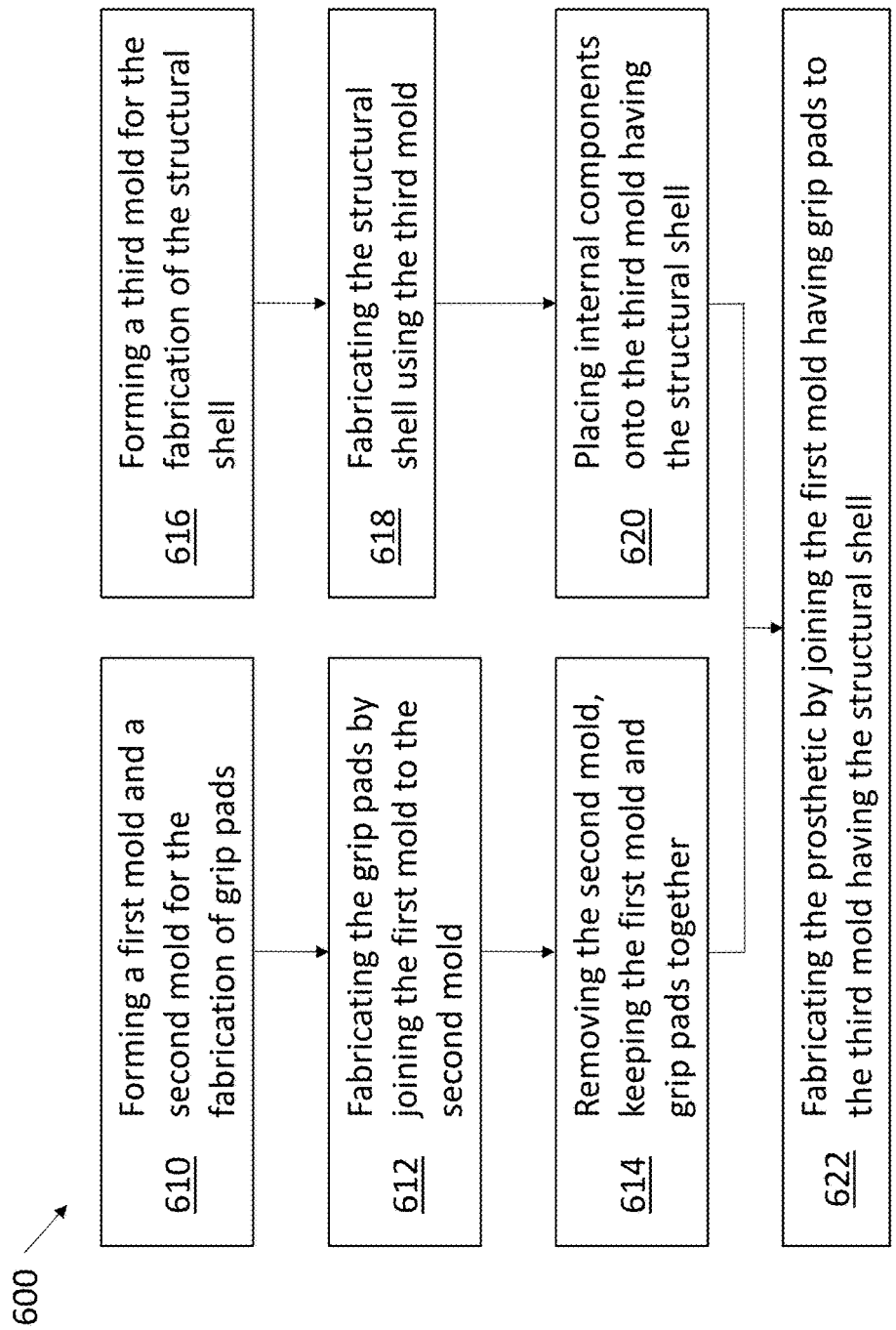
FIG. 28 is a flowchart illustrating an exemplary additive manufacturing molding method.

Referring now to FIG. 28, an exemplary method 600 is depicted. The method uses a plurality of 3D printed molds. For example, three molds may be used: a first mold and a second mold to fabricate grip pads (step 610), and a third mold to fabricate the structural shell (step 616). In one embodiment, the molds are created from customized finger geometry, such as in computer aided design (CAD) software. Parameters such as length, thickness, and joint stiffness can be directly altered for each user. In one embodiment, the mold is split along the gripping surface lines and a parting line analysis is done to minimize undercuts. Significant undercuts can result in die lock, preventing the removal of the solid part from the mold. If necessary, the mold can be split lengthwise and printed in two parts with bolting features that can be removed if die lock occurs. In one embodiment, the mold is printed using VeroClear material. In another embodiment, the mold is printed using ABS plastic. In one embodiment, the printed molds are covered with a wax-based or polyvinyl alcohol (PVA) mold release.

To fabricate grip pads, the first mold and the second mold are joined together and filled with grip pad material (step 612). For example, a urethane material may be placed between the first mold and the second mold. In one embodiment, the urethane material may be placed in a vacuum chamber before placement in the mold to degas the material and prevent grip pad defects. In one embodiment, the second mold may comprise features such as risers and air vents to release excess trapped gases. After the grip pad material has cured, the second mold is removed and excess grip pad material is trimmed from the grip pads (step 614).

To fabricate the structural shell, structural shell material is used to line the third mold (step 618). For example, carbon fiber dry cloth may be layered onto the third mold and epoxy resin flooded over the carbon fiber. The mold may then be inserted into a silicon vacuum bag to remove excess epoxy resin and to apply pressure over the mold. After the epoxy resin has cured, the mold is removed from the vacuum bag and excess structural shell material is trimmed from the structural shell.

To fabricate the prosthetic component, the first mold having the grip pads is joined to the third mold having the structural shell (step 622). If a sophisticated internal structure is desired, such as cable guides or other components, these components may be added to the third mold having the structural shell prior to joining the third mold with the first mold (step 620). For example, epoxy expanding foam may be injected into the mold to fill in the space between the grip pads and the structural shell. The expanding epoxy foam core bonds the components together. PVA mold release may be used to cover surfaces of the prosthetic component to protect it from bonding with the epoxy. After the epoxy has cured, the first mold and the third mold are removed, and the component may be trimmed or sanded to the user's preference.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

The Body-powered Anthropomorphic Prosthetic Hand, Mechanical Coupling Methods

The following example demonstrates the development of a prosthetic hand featuring a mechanical coupling mechanism that enables proper force distribution from a body-powered cable to the four fingers of the hand for both a power and precision grasp. This variation in grasping behaviour is selected through a mechanical lever placed on the outside of the hand. By placing this lever on the side of the hand, the user can simply switch between power and precision grasp situations using an able hand or by contact with another object in the environment such as a table edge. The following example also demonstrates a mechanical coupling method tuned for lateral, precision, and power grasps similar to those achieved in the current state-of-the-art prosthetic hands but achieved mechanically for use in body-powered devices.

Adaptive Grasping Behavior

By coupling the fingers together though a differential mechanism, the finger motion is not restricted when one finger or link makes contact. Instead, all the fingers are able to close until contact is made. This behaviour has shown to be extremely helpful in power grasping and grasps that envelope an object. Even state-of-the-art myoelectric hands with actuators on each finger use a similar grasp closing method. The iLimb, Bebionic, and Vincent hands rely on current control to achieve the proper force distribution during power grasping. The present strategy is to run each of the motors to stall which allows each of the fingers to make contact on an irregular shaped object. The various grasp types are achieved by selectively altering the rest position and the speed of closing for each finger. The same method of driving each finger until contact is made can be achieved mechanically in a body-powered hand through the use of a differential coupling method.

Force Distribution Methods in Anthropomorphic Hands

Figure 22:
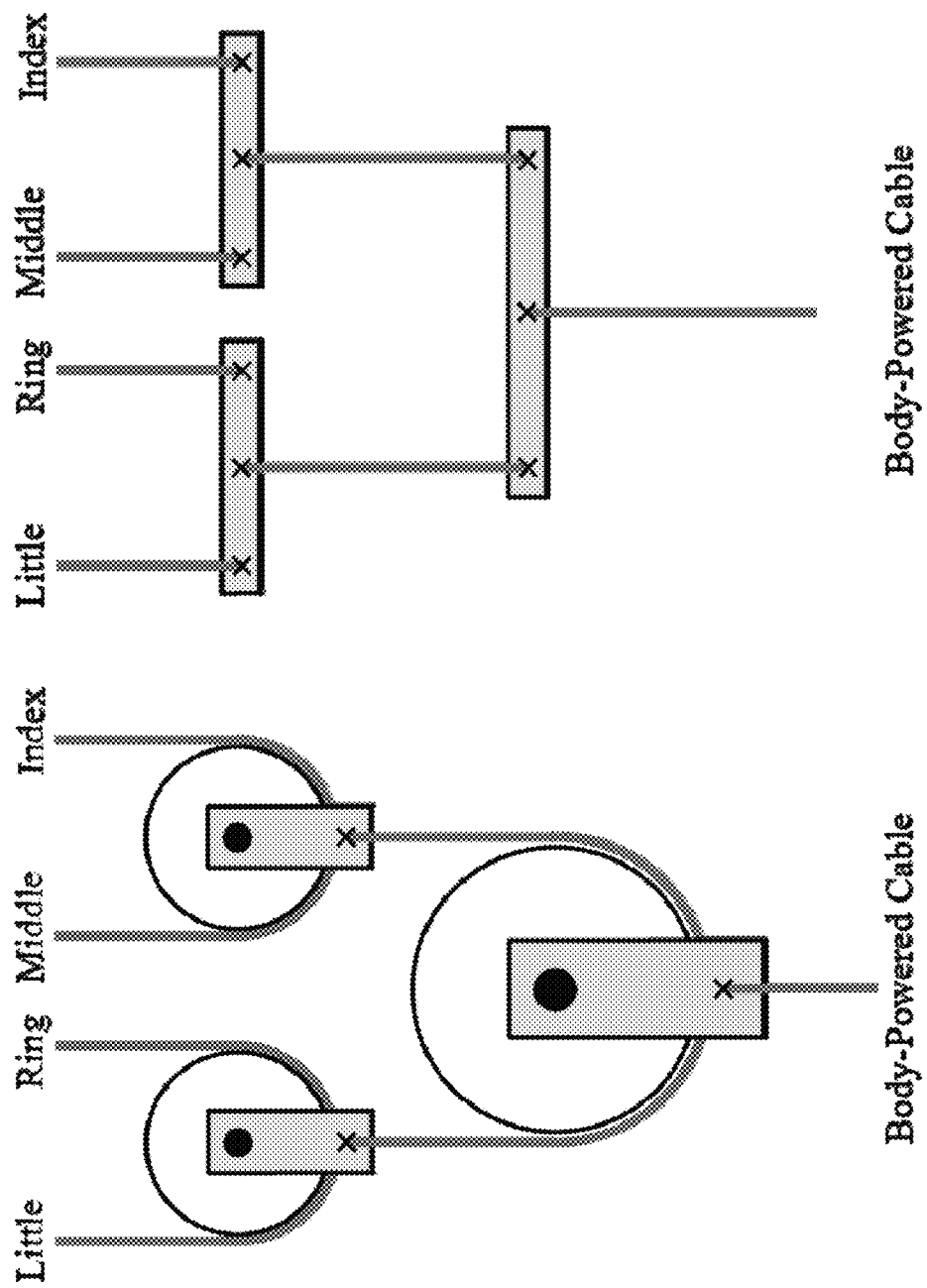
FIG. 22 is a schematic demonstrating typical underactuated differentials for tendon driven hands using floating pulleys (left) or wiffle trees (right) to achieve force distribution that is independent of finger movement.

The most common way to distribute force from a single input such as a body-powered cable is through direct coupling of the five fingers. Underactuation can be used between the fingers to adapt to various shaped objects. A review of these types of distribution mechanisms can be found in Baril M et al., Proceedings of the ASME/IDETC/CEI, 2010. All of these methods distribute a single input to four or more outputs. FIG. 22 illustrates the common methods of achieving an underactuated grasp between the fingers of a tendon driven hand. An example of this type of coupling can be seen in Dollar A et al., Int J Robot Res, 2010, 29(5):585 and Gosselin C et al., IEEE ICRA, 2008. The first method is by creating a series network of floating pulleys. Regardless of the position of any of the finger tendons, the force is equally distributed across all four tendons. The second method, shown in FIG. 22 (right) is a wiffle tree arrangement. Here, each of the floating bars is free to tilt to accommodate various finger positions at contact. With straight wiffle tree bars, the force is again distributed equally across all fingers.

Although equal distribution of the gripping force across all four fingers of the hand is beneficial for power grasping, equal distribution is not desirable when performing a precision grasp, or any other grasp that involves any finger not making contact with the object. For example, when performing a precision grasp, it is better to directly control the motion of the index finger as a function of the body-powered cable position. This gives better control and feel for the force being place on the single finger if contact is only occurring between the index finger and thumb.

Figure 23:
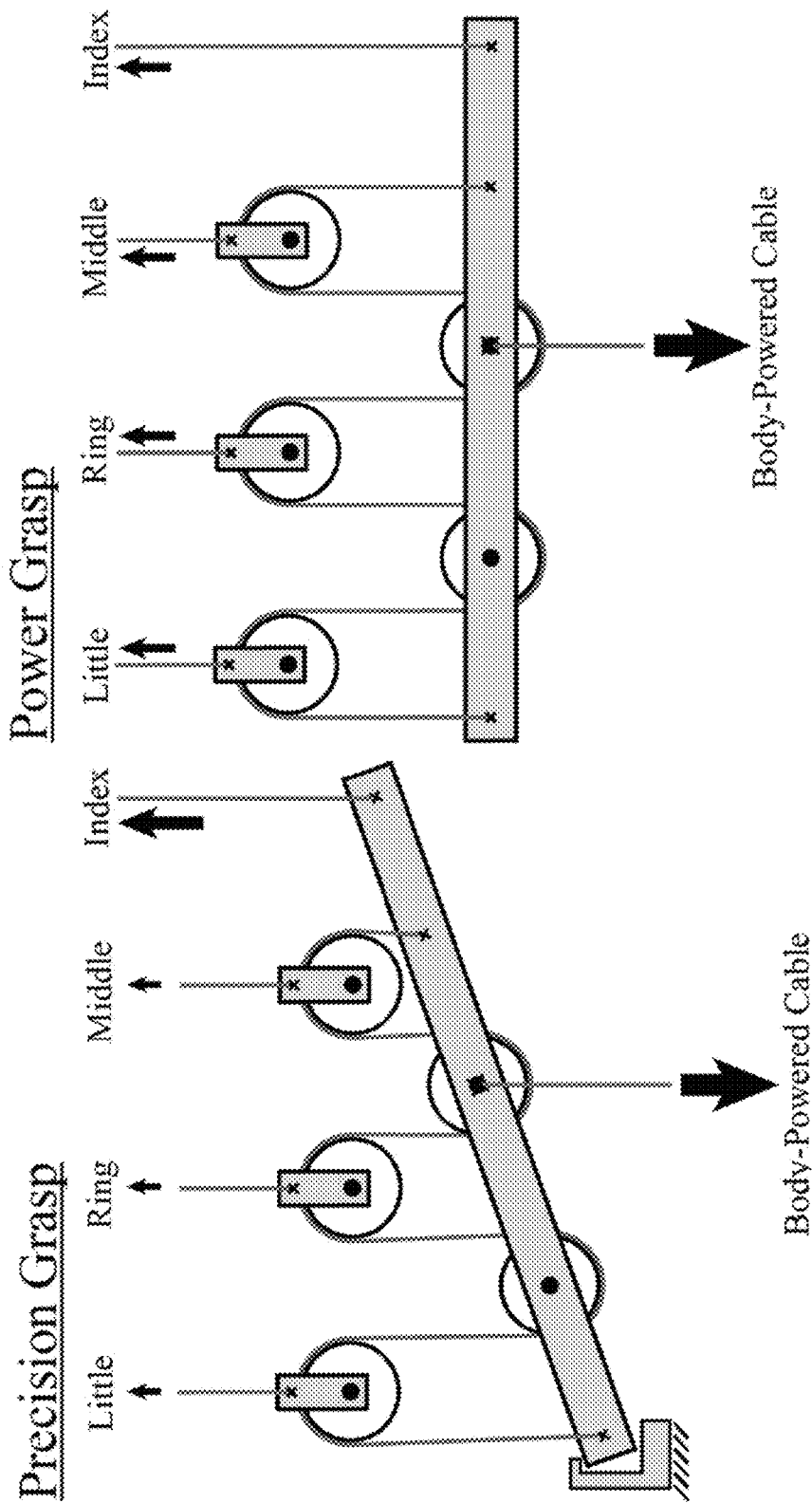
FIG. 23 is a schematic demonstrating a differential system using a combination of a single balance bar and pulleys to achieve equal force distribution during power grasping. When the bar is tilted and locked in the precision grasp position, the middle, ring, and little finger remain balanced while the index finger is directly coupled to the position of the body-powered cable.

A coupling design, shown in FIG. 23, is a combination of a single balance bar and floating pulleys connected to the body-powered cable at the center. The index finger actuation cable is fixed to one end of the bar. The actuation cables for the middle, ring, and little finger are attached to floating pulleys. All of the floating pulleys are coupled to the balance bar with a single tendon that spans two additional pulleys attached to the balance bar. Any difference in position of the middle, ring, and little finger can be taken up through movement of the pulleys on the tendon. Any difference between the position of the index finger and the average position of the middle, ring, and little finger results in the entire floating balance bar tilting in either direction. At any point in this motion, the force is still distributed equally among the four fingers.

Figures 24A, 24B, 24C, 24D:
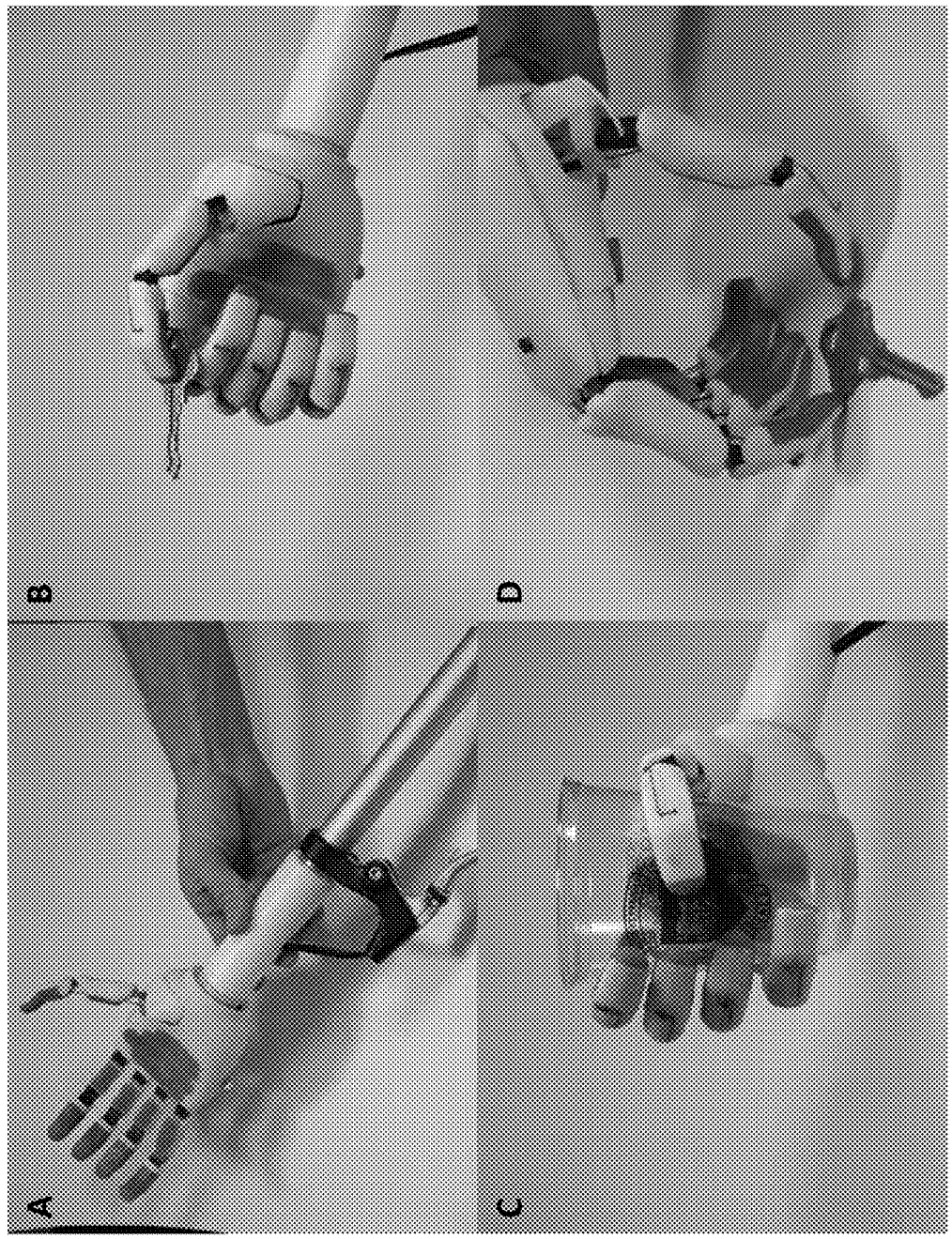
FIG. 24A through FIG. 24D, depicts an exemplary prosthetic hand being evaluated using an able body simulator that mimicked the movement of the body-powered actuation cable. The hand is shown in (FIG. 24A) a relaxed state, (FIG. 24B) a lateral grasp configuration, (FIG. 24C) a power grasp configuration, and (FIG. 24D) a precision grasp configuration.

When a precision grasp is desired, a small protrusion on the side of the hand is pulled downward and latched. This motion locks the left side (the side opposite the index finger) of the balance bar in the most downward position. The result is shown in FIG. 23. Since the bar is now constrained to pivot about the latching point, the movement of the index finger is now a direct function of the position of the body-powered cable. In addition, since the index finger and the set of middle, ring, and little fingers are now decoupled, more force from the body powered harness is now transferred into the index finger instead of the force being shared equally between the four fingers. FIG. 24 shows the force distribution between the four fingers in relation to the body powered harness for both the power and precision grasp configurations. The precise distribution of forces can be altered by changing the spacing between the output tendons on the balance bar.

Implementation in Prosthetic Hand

Figures 21A, 21B:
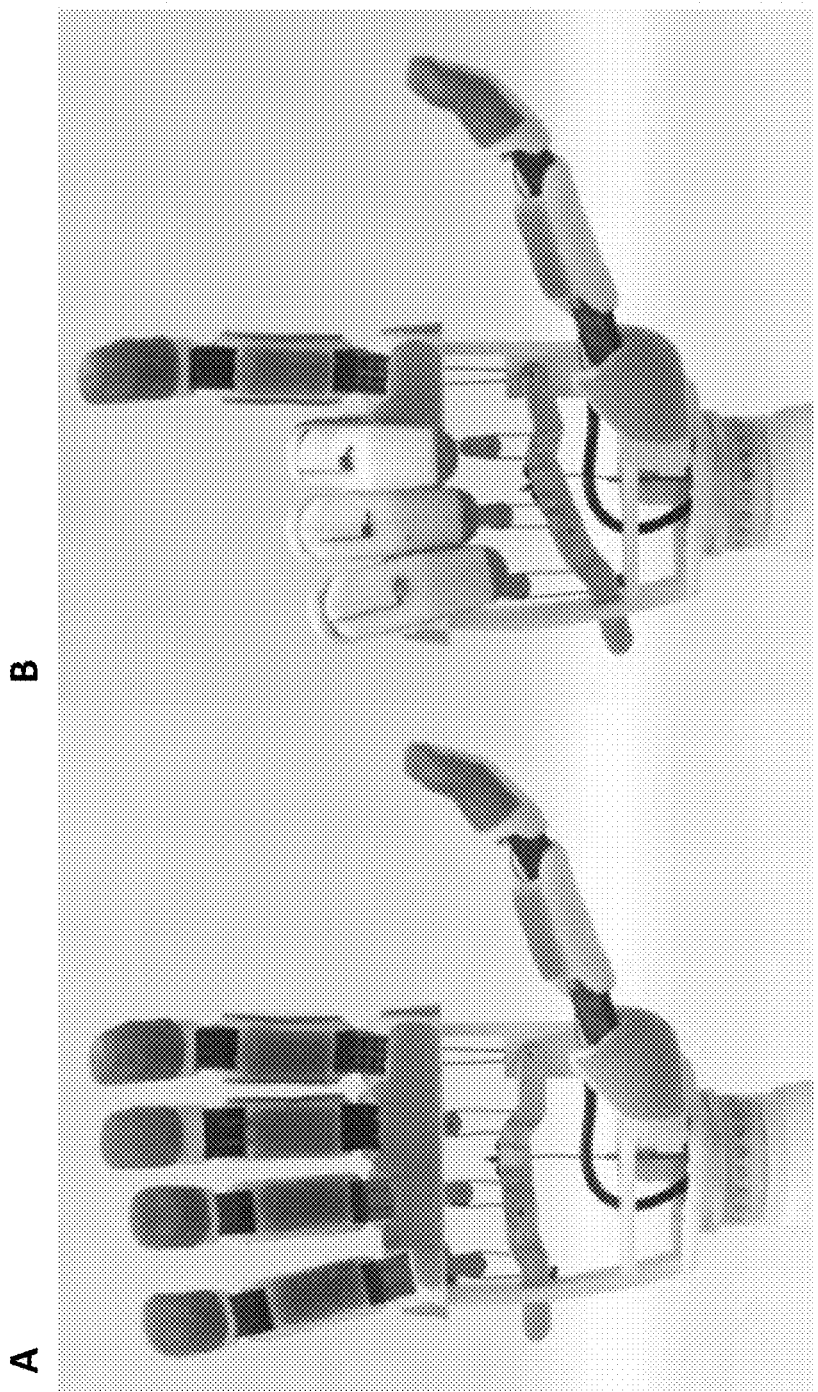
FIG. 21A and FIG. 21B, depicts the prosthetic hand and single balance bar mechanism in (FIG. 21A) a power grasping configuration and (FIG. 21B) a precision grasping configuration.

A prosthetic hand was fabricated to test and evaluate the coupling strategy. FIG. 21A and FIG. 21B show the prosthetic hand in the power and precision grasp postures with the front and back cover removed to expose the balance bar coupling mechanism. This prosthetic hand has two joints in each finger with a single tendon spanning both joints of each finger. The joints of the hand are made of a urethane flexure material similar to those used in the OpenHand (Ma R R et al., IEEE ICRA, 2013). The use of flexure joints helps to improve the adaptability by adding additional out of plane compliance to each finger. All hand components were made from ABS plastic with the balance bar and floating pulleys fabricated from aluminium.

Coupling of Thumb Movement

A common observation is that various grasp types require different motion paths of the thumb. For the prosthetic hand, the thumb was placed on a passive circumduction axis that allowed a user to place the thumb in one of three positions to perform a lateral, precision, or power grasp. The thumb flexion actuation tendon was directly fixed to the main body powered cable without any adaptability. This was done to ensure a force balance across the objects being grasped in the hand during power, precision, and lateral grasps.

Testing and Evaluation

FIG. 24 shows an example of the ability of the prosthetic hand in power grasp to adapt to a wide variety of object shapes. The prosthetic hand was tested with able body subjects using a simulator that mimicked the actuation of a single body powered cable. Although this is not a true measure of hand function, the system allowed for a better study of the grasping behaviours of the hand with a single input tendon. This system was also evaluated using the Southampton Hand Assessment Procedure (SHAP) test to give a wider range of objects and activities of daily living (ADL) tasks. The results of this test are positive but strictly qualitative since it was performed by an able person without a true body-powered harness. The alteration of the coupling method was important to maintain a stable and predictable precision grasp.

Integrated Grasp Selector for Multiple Grasp Types

Figure 26A:
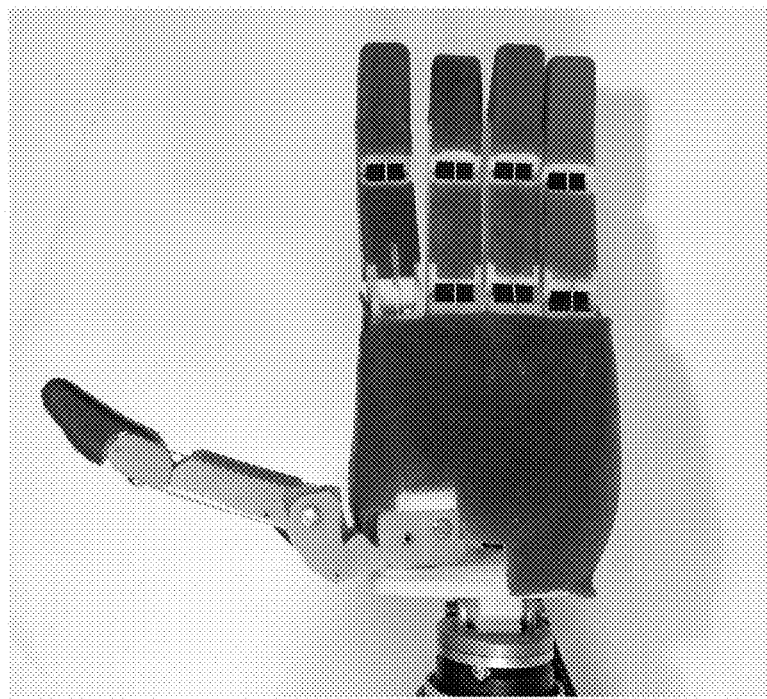
FIG. 26A through FIG. 26C, depicts an exemplary prosthetic hand demonstrating three distinct positions of the thumb.
Figure 26B:
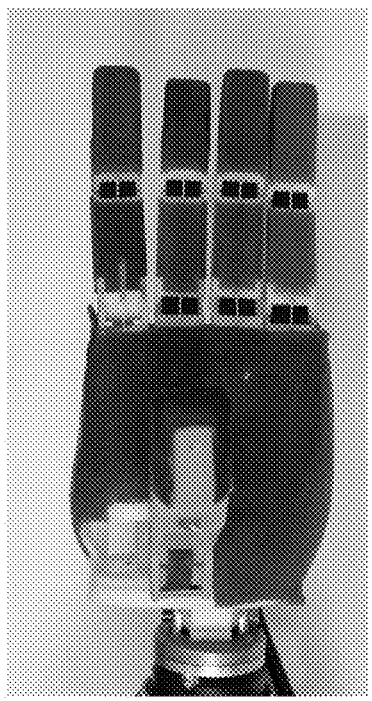
Figure 26C:
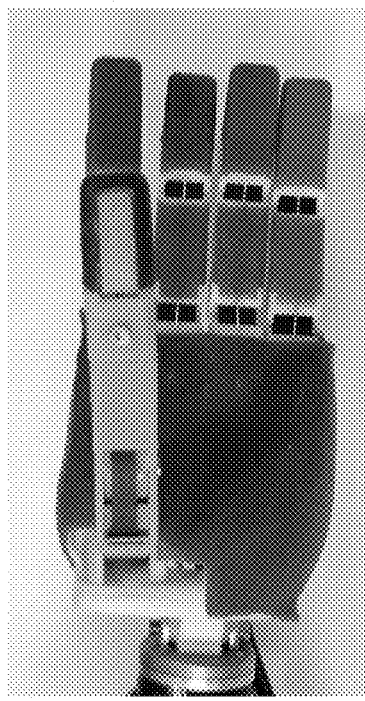

After showing the benefits of the grasp specific coupling strategy, a body-powered anthropomorphic hand was developed that was capable of achieving lateral, precision, and power grasping through the use of an integrated mechanical coupling mechanism. Prior to grasping, the user simply places the thumb in the position associated with the desired grasp type (similar to what was required in the first prosthesis). The movement of the thumb (which can be achieved by an able hand or through contact with the environment) acts like a mechanical selector to alter the pre-grasp position, closing speeds, and overall force distribution from the body-powered cable to the five fingers of the hand. Others have used mechanical selectors to change the grasp type (Baril M et al., J Mech Design, 2013, 135(121008):1-7) but none have associated this change with a movement of the thumb. FIG. 26 shows the prosthetic hand with the three distinct position of the thumb which internally affects the coupling strategy from the body-powered harness to the five fingers. These properties of the force distribution and closing rates were experimentally tailored to give the best possible finger behaviours for each individual grasp type.

A high degree of adaptability was shown during power grasping with additional control of the index finger during precision and lateral grasping. In addition, latching the balance bar was found to allow the user to have an index finger point. This was useful for delicate tasks such as typing and pushing buttons. Without the altered coupling strategy, precision grasping was difficult since the middle, ring, and little finger would continue to reconfigure even after the precision grasp was established on the object.

Example 2

Fabrication of Lightweight Custom Composite Prosthesis Using Additive Manufacturing Molding Techniques Additive manufacturing, or 3D printing, has become a widely accessible and cost-effective method of prototyping due to its ability to quickly create custom modeled parts out of inexpensive thermoplastics and resins. A common method of additive manufacturing, fused deposition modeling (FDM), uses an extruder head that lays down a filament in discretized layers to create a final part. The thermoplastic filament, acrylonitrile butadiene styrene (ABS), is commonly used in this process due to its high impact resistance, toughness, and light weight. This has made 3D printed ABS a prevalent choice for open-source prosthesis hands with products like the Cyborg-Beast or the Raptor Hand (Zuniga J et al., BMC Research Notes, 2015, 8(1):10; Enabling the Future: Upper Limb Prosthetics. Available: http://enablingthefuture.org/upper-limb-prosthetics Mar. 25, 2015). The modularity and variety of the open-source market allow for the customization of upper-limb prosthetic terminal devices helping the impaired regain hand function to the best of their ability while maintaining a low cost. Although 3D printing has made custom prosthetic designs accessible to the public, it lacks in durability and grip compared to commercially manufactured terminal devices.

Figure 27:
FIG. 27 depicts fingers from the Cyborg Beast hand (top), the Bebionic v3 (left), and composite prosthetic finger created using the additive manufacturing molding technique (right).

The following example investigates the current manufacturing methods of both open-source and professional prostheses. This example further introduces a new method that bridges the gap between highly customizable open-source 3D printed prosthetic hands and the professional prosthetic hand market. This method results in finger/hand components that are lightweight, durable, and include gripping surfaces like those used in the professional prosthetics market (FIG. 27). Results of strength tests are shown to compare the various manufacturing methods to support the new method. The goal of this method is to improve and refine future terminal device designs to create a cost-effective, customizable, durable, and lightweight prosthetic hand.

Current Manufacturing Methods

3D Printing—FDM

The current fabrication process for open-source prosthetic hands includes modeling the solid part geometry in a computer aided design package (CAD) and then 3D printing it in ABS or polylactic acid (PLA) plastic (Enabling the Future: Upper Limb Prosthetics. Available: http://enablingthefuture.org/upper-limb-prosthetics Mar. 25, 2015) using the most common FDM printing technique. The printing software allows the users to determine the infill amount, therefore allowing the part to be printed partially hollow to save material and reduce weight at the expense of a potentially weaker component. A significant advantage of FDM printing of prostheses is that it allows users to quickly customize the shape and size of components to fit an individual patient. For open source hands like the Cyborg Beast Hand, these components are made available online for anyone to print or scale as needed, which is useful when children quickly grow out of their prosthetic terminal devices (Enabling the Future: Upper Limb Prosthetics. Available: http://enablingthefuture.org/upper-limb-prosthetics Mar. 25, 2015).

One current limitation to FDM printing is the limited number of materials available. When part strength and stiffness is a requirement most 3D printed parts and materials fall short since they are mostly limited to thermoplastics. Attempts have been made to reinforce 3D printed parts to make them more durable; however, this only provides marginal improvements (Belter J T et al., Intelligent Robots and Systems (IROS 2014), 2014 IEEE/RSJ International Conference on IEEE, pp. 2886; Jamalabad V R et al., In Proceedings of Solid Freeform Fabrication Symposium, 1996; Zonder L et al., White Paper by Stratasys Inc., 2013. Available: http://www.stratasys.com/~/media/Main/Files/White%20Papers/SSYS-WP-InjectionMolding-9-23-13.pdf). New printing methods are also being implemented that allow for the 3D printing of composite structures with Kevlar and Carbon Fiber (MARKFORGED: A new class of 3D printing materials. Available: https://markforged.com/materials Feb. 2, 2015). Although this method may prove beneficial in the future, its processes are currently still under development.

Professional Prostheses

The current fabrication process for commercially available prosthetic hands includes a combination of injection molded plastic and casted or machined metal components. The materials include glass-filled Nylon, titanium, and aluminum (RSLSteeper Bebionic3: The Hand. Available: http://www.bebionic.com/the_hand Mar. 1, 2015; Touch bionics i-limb ultra: Key Features. Available: http://www.touchbionics.com/products/active-prostheses/i-limb-ultra/key-features Mar. 1, 2015). Urethane rubber grip pads are injection molded and adhered to the surface of the finger tips and palms to increase the grip of the smooth metal or plastic. All joints (usually pin points) are assembled, and connected to the aluminum or steel frame and then attached to the actuation system.

The major limitation of this method is that machined titanium or aluminum components are expensive, and the tooling required for Nylon injection molded components limits the customizability of the design. It is likely that only a small number of sizes of the hands are available due to the large tooling cost associated with another size option and customizable features specific to each patient are not possible. For example, the i-limb Ultra myoelectric prosthetic hand is only available in sizes medium and small (Touch bionics i-limb ultra revolution. Available: http://www.touch-bionics.com/sites/default/files/i-limb_ultra_revolution_datasheet.pdf Feb. 5, 2015).

Custom Composite Prostheses Using Additive Manufacturing Molding Techniques

The additive manufacturing molding technique creates custom composite components utilizing 3D printing to produce professional grade prosthetic components while maintaining the customizability for individual patients. This method is perfect for prosthetic hand fabrication since the personal nature of prosthetic hands requires frequent design changes and customization for each patient.

Overview

The influence for the material composition of our composite prosthetic hand is derived from the manufacturing of ultra-lightweight structural components used in Formula 1 racecars and aerospace components. Here, composite materials with various core structures are used to crate materials with the highest possible strength to weight ratios. Typical carbon-fiber techniques are rarely used on components as small as prosthetic hands or fingers due to the part contour complexity. The present method of fabrication has overcome many of the previous limitations and allows for the fabrication of prosthetic fingers with the same materials and techniques used in high grade aerospace components.

The desired prosthetic finger composition consists of three main layers; the carbon-fiber structural shell located on the back and sides of the finger, a lightweight foam filler material that serves to bond the internal components together, and a soft urethane grip surface that mates seamlessly with the shape of the structural shell. Each of these individual elements, as well as the fully assembled finger, can be fabricated through the use of three custom molds. Mold A consists of the geometry of the front of the finger up to the parting line between the grip surface and the carbon-fiber structural shell. Mold B mates together with Mold A and forms the inside surface of the urethane grip pad. Mold C mates together with Mold A but forms the back outer surface of the finger. An illustration of the three molds is shown in FIG. 29.

Custom 3D Printed Mold Fabrication

The present method uses multi-part molds created from customized finger geometry. First, the desired finger geometry is created in CAD software. The parameters such as length, thickness, and even joint stiffness can be directly altered for each patient. A set of small molds are then automatically created from the desired finger geometry.

The mold is then split along the gripping surface lines and a parting line analysis is then done to minimize undercuts. Significant undercuts can result in die lock, preventing the removal of the solid part from the mold. If necessary, the mold can be split lengthwise and printed in two parts with bolting features that can be removed if die lock occurs. The molds are then printed on an Objet printer using VeroClear material (RedEye: Veroclear. Material Data Sheet. Available: http://www.redeyeondemand.com/veroclear/ Feb. 3, 2015). Alternatively, the molds can be printed in ABS using a standard FDM printer. The actual material strength of the mold is not important. However, thin walls can lead to potential deformations in the finger geometry. This results from the internal pressure build-up of the expanding foam during the final in-mold assembly step.

Fabrication of Individual Elements

After the three molds have been printed, they are covered with a wax-based or polyvinyl alcohol (PVA) mold release. Molds A and B are brought together to create the geometry of the grip pads on the anterior side of the fingers. To prevent grip pad defects, it is important for the urethane material to be placed in a vacuum chamber before being placed in the mold to degas the resin. In case inconsistencies persist in the final part, it is recommended to incorporate risers and air vents into the Part B mold to release excess trapped gases. After the urethane material has cured, Part B is removed and excess flashing or riser material is trimmed from the grip pads.

Figure 30:
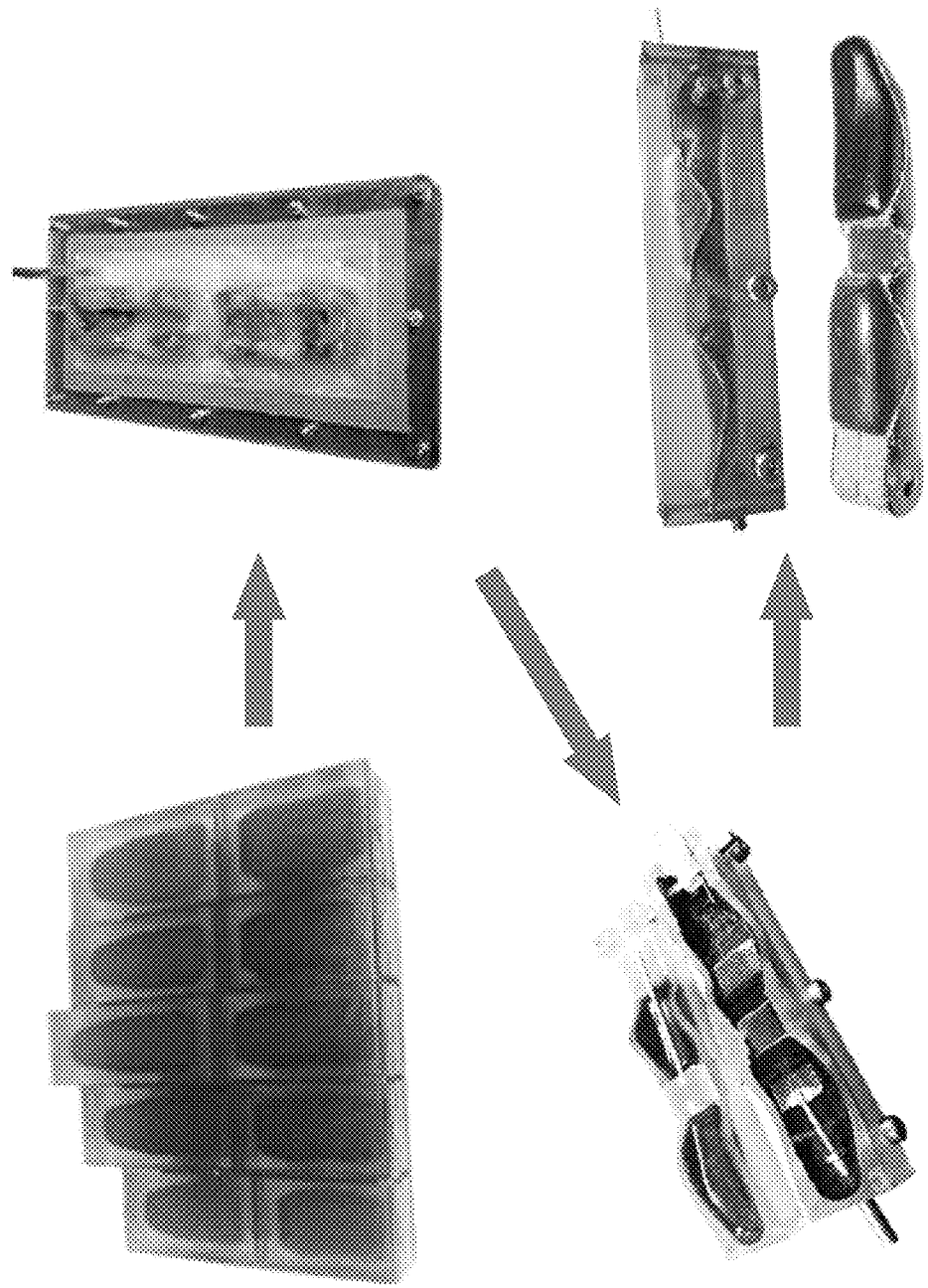
FIG. 30 depicts images of each step of the multi-step manufacturing process for fabricating a composite finger using 3D printed molds.

Immediately after the grip pads are cast, the carbon fiber half of the mold, denoted as Mold C in FIG. 29, should be prepped with a PVA mold release. Two layers of 200 gsm 3 k 2×2 twill weave carbon-fiber dry cloth is placed in the mold and trimmed to the appropriate size. To improve overall strength, the orientation of the carbon weave should be offset by 45 degrees between the layers. Epoxy resin is then flooded over the dry carbon-fibers. A custom silicon vacuum bag, as seen in FIG. 30, is then placed over the wet carbon to remove excess resin and apply pressure to the inside surface of the mold. Once the epoxy resin has fully cured, the vacuum bag and absorption layers are removed and the carbon shell is trimmed to the edges of the mold.

Full Mold Assembly and Final Finger Fabrication

Next, all the previous components are integrated into one final part using Molds A and C and additional inserts. Before closing the mold, all the necessary inserts and joints are placed in the correct locations. Epoxy expanding foam (Sicomin PB400; Sicomin Technical Datasheet: PB 250, PB 400/SD 560× Resilient % ambient curing epoxy foam 2014.

Available: http://www.sicomin.com/datasheets/product-pdf203.pdf Mar. 3, 2015) is poured in the middle of the two halves to join the shell and the grip pad to make a finger. The expanding epoxy foam core acts as a lightweight internal structure and a glue to bond all the components together. Carefully painted PVA mold release was used to prevent the expanding foam from bonding to selected surfaces such as the center of the flexible urethane finger joint. It is acceptable to allow some of the foam to overflow in this process to reduce pressure and purge additional air. After the recommended amount of curing time, the finger can be removed and lightly sanded to remove any flashing from the parting line.

This finger is durable with its carbon fiber shell 209 but also very light with its foam core, which bonds joint members and other additional inserts into the finger. The resulting fingers, seen in FIG. 32, have grip pads to improve grasping capabilities, flexure joints to promote out of plane bending, and outer carbon shells for added strength and durability. Different inserts such as pin joints, tendon tensioning mechanisms, and PEEK tubing to reduce tendon friction are used in these finger examples. The palm structure of the hand is fabricated in a similar process.

Evaluation of Composite Finger Made with Additive Manufactured Molding

Three different measures were used to evaluate the performance of the manufacturing method as well as other manufacturing methods commonly used in prosthetic hands. These methods included a strength analysis, weight analysis, and a discussion of the advantages and disadvantages of the composite molding process. The core materials we will test include 3D printed ABS plastic in both solid and sparse raster filled, epoxy expanding foam, and carbon-fiber composite structures. For reference, information on the strength of aluminum 6061 will be included since it is also a common material used in commercial prosthetic hands.

Strength Analysis

To evaluate the relative strength of each manufacturing method, rectangular bar specimens were tested using the ASTM D790 flexural three-point bending test (ASTM D790, "Standard test method of flexural properties of unreinforced and reinforced Plastics and electrically insolating materials", ASTM.org, ASTM International). For each manufacturing method, five specimens were tested. The specimens were rectangular blocks measuring 8.3×19.1×152.4 mm and were sized according to the standard. When testing 3D printed ABS plastic, the layer direction was noted to evaluate the effect of different printing orientations. In a horizontal test the specimen width was parallel with the print tray and extruder layer orientation, while in vertical tests the sample width was oriented vertically on the print tray. For the carbon-fiber shell test specimens, the carbon-fiber was placed on the top and bottom of the foam. No carbon-fiber was placed on the sides of the specimen to better replicate the open shell of the fingers in from the manufacturing method.

Figure 33:
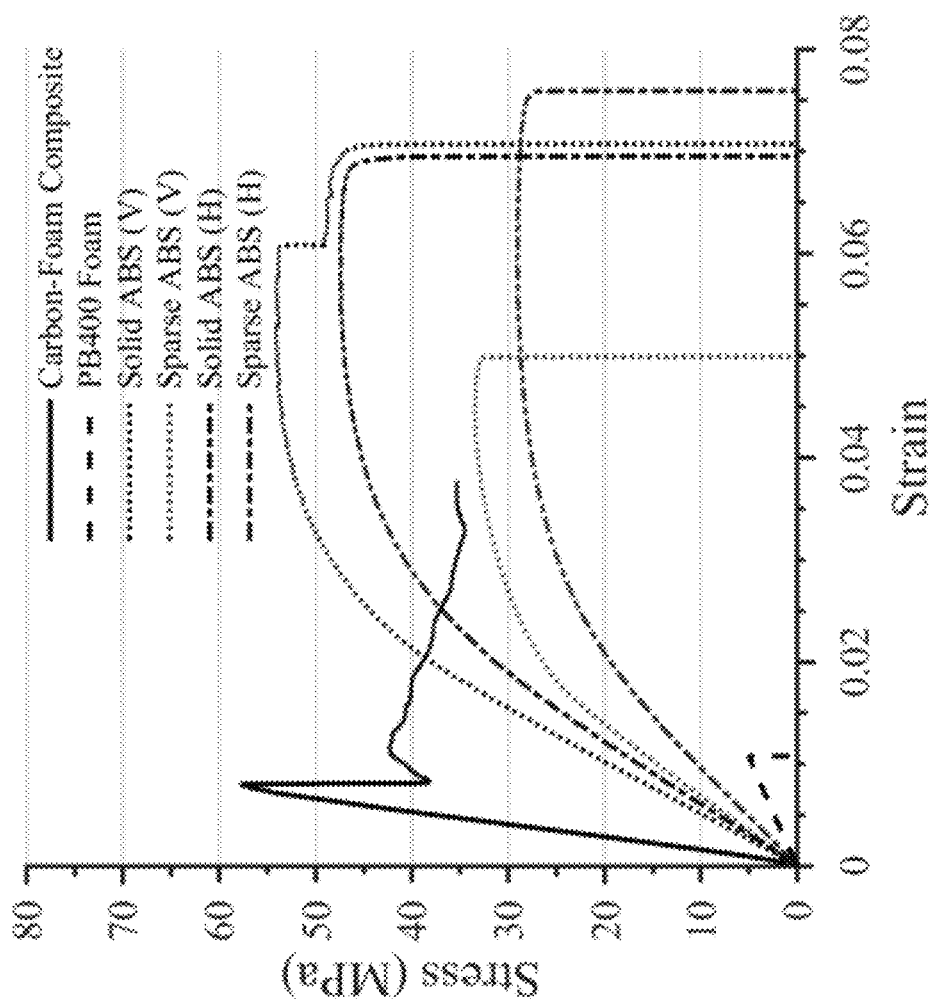
FIG. 33 depicts a graph showing the stress-strain relationship for each specimen. Two layer carbon fiber with PB400 expanding epoxy foam internal core, PB400 expanding foam, solid printed ABS vertical (V) and horizontal (H) print, and sparse printed ABS vertical (V) and horizontal (H) print. All samples were tested to failure.
Figure 34:
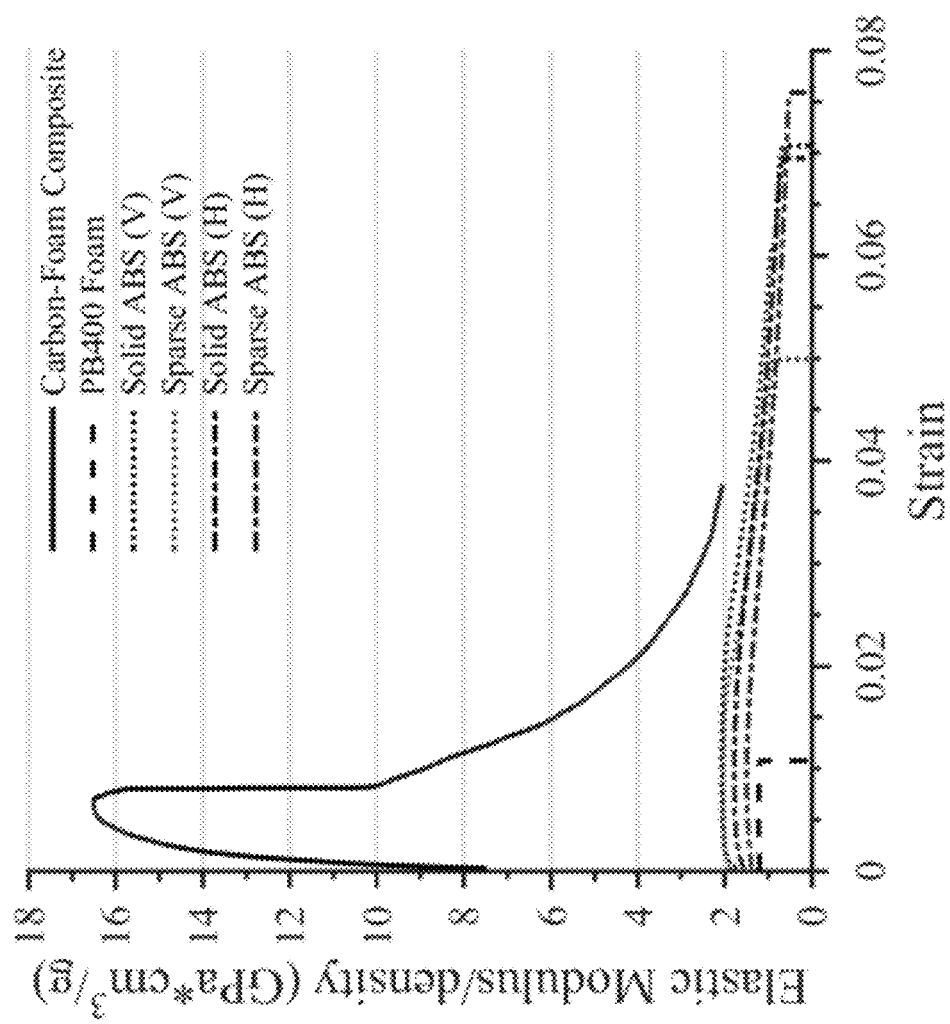
FIG. 34 depicts a graph showing the stiffness to weight ratio for each test specimen. Two layer carbon fiber with PB400 expanding epoxy foam internal core, PB400 expanding foam, solid printed ABS vertical (V) and horizontal (H) print, and sparse printed ABS vertical (V) and horizontal (H) print. The ratio is determined by the elastic modulus at a given strain divided by the specimen's density.

In order to compare the different materials, each specimen's weight and density were recorded; the stress during the three point bending test was also calculated. A stiffness to weight ratio was then determined for each specimen in order to evaluate the optimal material, shown in FIG. 31. The stress-strain relationship for each specimen is shown in FIG. 33. The stiffness to weight ratio is plotted versus strain as shown in FIG. 34. It is seen that the epoxy expanding foam has the lowest average weight of 9.25 g, but also has the lowest stiffness to weight ratio. The carbon-fiber with epoxy expanding foam specimen has the next lowest average weight of 11.3 g, and also has a significant stiffness to weight ratio of 1.65 GPa*cm$^3$/g. This ratio demonstrates the added strength and durability of using carbon fiber, with the low weight of the epoxy expanding foam. The calculated values from 6061 aluminum were based on known material properties found in (Aluminum 6061-T6; 6061-T651 Material Properties, Matweb.com, Available: http://www.matweb.com/search/DataSheet.aspx?MatGUID=1b8c06d0ca7c456694c7777d9e10be5b&ckck=1).

Weight Analysis

To evaluate the weight of the fingers, equivalent models were fabricated of a 50$^{th}$ percentile female sized middle finger. The proximal and distal links of each finger were connected with a urethane flexure (Smooth-On PMC; Smooth-On PMC-780 Urethane Rubber. Available: http://www.smooth-on.com/tb/files/PMC-780_Dry-Wet.pdf Mar. 3, 2015) and a two layer grip surface (Smooth-On Vytaflex; Smooth-On Vitaflex Series Urethane Rubber. Available: http://www.smooth-on.com/tb/files/Vytaflex_Series_TB.pdf Mar. 3, 2015) was added to each finger. For the epoxy foam core fingers, the grip pads and flexures were molded and embedded into the foam, while for the 3D printed parts, grip pads and flexures were bonded on using adhesive. The quantity of adhesive was measured out to be 0.3 additional grams for the ABS printed fingers shown in FIG. 35. The finger weight was estimated for the machined aluminum finger using the total volume of the finger CAD model and the density of aluminum (Aluminum 6061-T6; 6061-T651 Material Properties, Matweb.com, Available: http://www-.matweb.com/search/DataSheet.aspx?MatGUID=1b8c06d0ca7c456694c7777d9e10be5b&ckck=1). The weight of each finger fabricated with each respective material is shown in FIG. 35. The expanding epoxy foam with and without carbon fiber maintain the lowest weight, with a weight of 8.6 and 8.5 grams respectively. The aluminum is almost four times the weight of the foam fingers, having a weight of 31.6 g, however, it is unlikely that aluminum fingers would be fabricated to be solid aluminum.

Molding Advantages

One advantage of additive manufacturing is the ease of production. A custom model can go straight from design to manufacturing in a matter of hours. Although additional time is required, the durability of a solid printed finger is similar to that of the composite though significantly heavier. The main advantage of machined aluminum is the strength of the material. Complex 3D geometries are difficult to machine with computer numerical control (CNC) mills and require multiple readjustments.

The main advantage to the carbon fingers was the durability of the finger with respect to weight. It was also relatively easy to manufacture as the carbon shell and grip pad could be made at the same time. Without removing each from their respective molds, the two parts making up the outer layers could be sealed together with foam. The carbon shell presented additional advantages such as abrasive resistance as well as a clean surface finish that can be an issue with 3D printed parts and fingers made completely from expanding foams.

Summary

The present manufacturing method was found to create a durable and lightweight prosthetic finger. Although the method may be more complex than machining or 3D printing, the benefits of reduced weight in the prosthetics community are very important (Pylatiuk C et al., Prosthet Orthot Int. 2007, 31(4):362-70). A full hand made out of carbon laminate using the method could potentially be one half the weight of a 3D printed hand and one quarter the weight of a machined aluminum hand. For amputees, the prosthetic hand is an extension of their body. Reducing the weight of the prosthetic can not only help prevent fatigue but can also aid grasping by allowing for easier and quicker movements.

The ability to work in parallel when curing the grip pad urethane and carbon fiber resin allows the process to be simplified in four steps: (1) creating molds, (2) casting urethanes and laying carbon fiber, (3) creating foam core, and (4) removing the final finger from the molds. The downtime associated with letting resins cure is shared during the production of the carbon fiber and gripping surfaces. This allows the manufacturer to create any necessary inserts for the mold and the finger, such as a urethane flexure joint, while the first two parts are curing. This efficiency is one of the advantages of the present composite finger manufacturing process.

If weight, customizability, and cost were not important factors, a machined aluminum finger would be the primary option due to its superior strength and durability. The use of composites in prosthetic fingers provides a significant stiffness to weight profile over that of aluminum and solid ABS plastics. At low strains, we saw that the composite finger made using the present method was almost 8 times stiffer than solid and sparse printed ABS plastic. A more durable finger for a given weight allows the user to have the same sturdiness with less fatigue or force required to maneuver the finger.

As additive manufacturing becomes more available, the present method can reach out of prostheses into broader categories like custom lightweight robotics. Rapid prototyping with additive manufacturing allows the user to visualize the size and geometry of the part. As a prototyping technique, the present method can provide the fabricator with a useable and rapidly alterable prototype that can simulate the durability of the final product. The rapid manufacturing of molds to create composites can impact many industries where a durable lightweight replacement part is needed quickly or where access to heavy machinery or casting equipment is limited.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A prosthetic hand device comprising:
a hand frame having a differential mechanism connected to an actuable index finger unit, at least one actuable secondary finger unit and an actuable thumb unit;
wherein the actuable thumb unit includes a plurality of lockable positions, wherein each lockable position corresponds to a different grasping configuration of the prosthetic hand; and
wherein the differential mechanism comprises:
a first bar having a pin joint at its midpoint and is coupled to at least one tendon line of the at least one secondary finger unit; and
a second bar coupled to an index finger tendon line and an index finger orientation cable at one end, to a thumb orientation cable at an opposite end, to a main actuation cable along its length, and to the pin joint of the first bar at a point between the second bar's midpoint and a thumb orientation cable coupling;
wherein movement of the first bar opens and closes the at least one secondary finger unit; wherein movement of the second bar opens and closes the index finger unit; and wherein an orientation of the thumb unit alters a configuration of the differential mechanism by applying tension on the thumb orientation cable and the index finger orientation cable.

2. The device of claim 1, wherein the at least one secondary finger unit, index finger unit and the thumb unit are passively held open by helical torsion springs and elastic flexure joints.

3. The device of claim 1, wherein the at least one secondary finger unit, index finger unit and the thumb unit comprise a removable pin.

4. The device of claim 1, wherein the thumb unit is lockable into alignment with the secondary finger unit for a power grasp.

5. The device of claim 4, wherein the prosthetic hand is configured to open and close the thumb unit, the at least one secondary finger unit, and the index finger unit.

6. The device of claim 1, wherein the thumb unit is lockable into alignment with the index finger unit for a precision grasp.

7. The device of claim 6, wherein the at least one secondary finger is configured to lock in a closed position and the prosthetic hand is configured to open and close the thumb unit and the index finger unit.

8. The device of claim 1, wherein the thumb unit is lockable into alignment with a side of the prosthetic hand for a lateral grasp.

9. The device of claim 8, wherein the at least one secondary finger unit and the index finger unit are configured to lock in a closed position and the prosthetic hand is configured to open and close the thumb unit.

10. The device of claim 1, wherein the prosthetic hand is actuated by a body-powered harness.

11. The device of claim 1, wherein the prosthetic hand is actuated by myoelectric control.

12. The device of claim 10 or 11, further comprising a grasp locking mechanism comprising a cable wrapped around a unidirectional rotating surface using friction to hold a grasp in place until the actuation is relaxed.

13. The device of claim 12, wherein the unidirectional rotating surface is a textured and contoured capstan pulley.

* * * * *